United States Patent [19]

Brown, Jr. et al.

[11] Patent Number: 5,472,859

[45] Date of Patent: Dec. 5, 1995

[54] ENZYMATIC METHOD FOR SYNTHESIS OF CELLULOSE 1

[76] Inventors: R. Malcolm Brown, Jr., 305 Skyline Dr., Austin, Tex. 78746; Shiro Kobayashi, 1-8-21, Yagiyama-minami, Taihaku-ku, Sendai, Miyagi, Japan; Krystyna Kudlicka, 1401 St. Edwards Dr. #148, Austin, Tex. 78704; Shigenori Kuga, 3-4-7 Mizukino, Moriya-machi, Ibaraki-ken, 302-01, Japan; Jong Lee, 3455 Lake Austin Blvd. #D, Austin, Tex. 78703; Likun Li, 1908 Carroll St., Apt. #1, Houston, Tex. 77030; Kazuo Okuda, 10-41 Ozu-cho #424, Kochi 780, Japan; Shin-Ichiro Shoda, 4-7-25-601, Chuo, Aoba-ku, Sendai, Miyagi, Japan

[21] Appl. No.: 100,868

[22] Filed: Aug. 2, 1993

[51] Int. Cl.$^6$ ............................ C12P 19/04; C12P 19/00; C12P 19/14; C12N 9/42
[52] U.S. Cl. ............................ 435/101; 435/97; 435/99; 435/176; 435/209
[58] Field of Search ........................... 435/101, 97, 99, 435/176, 209

[56] References Cited

U.S. PATENT DOCUMENTS 5,180,674  1/1993  Roth ........................................ 435/288

FOREIGN PATENT DOCUMENTS

| 87307891 | 9/1987 | European Pat. Off. . |
| 0260093 | 3/1988 | European Pat. Off. . |
| 3-103401 | 4/1991 | Japan . |
| 4-126090 | 4/1992 | Japan . |
| 4-121197 | 4/1992 | Japan . |

OTHER PUBLICATIONS

Bio Rad Catalog, p. 55 (1989).
Kobayashi et al., "Stereoselective Synthesis of Cellulose Catalyzed by Celluloase," *Polymer Preprints*, 38:3005–3007, 1989.
Kobayashi et al., "Synthesis of Cellulose with Cellulase Catalyst," *33rd IUPAC International Symposium on Macromolecules*, Jul. 8–13, 1990 (Montreal, Canada) Abstracts, Session 1.8.5.
Kobayashi et al., "Synthesis of Cellulose Catalyzed by Cellulase," *XVth International Carbohydrate Symposium*, Aug. 12–17, 1990 (Yokohama, Japan) Abstracts, p. 124.
Kobayashi et al., "Enzymatic Polymerization: the First in Vitro Synthesis of Cellulose via Non–Biosynthetic Path Catalysed by Cellulase," *American Chemical Society, Polymer Preprints*, 32(1):417–418, 1991, the meeting held in Atlanta, Ga.
Kobayashi et al., "Novel Method for Polysacchardie Synthesis Using an Enzyme: The First in Vitro Synthesis of Cellulose via Non–biosynthetic Path Utilizing Cellulase as Catalyst," *J. Am. Chem. Soc.*, 113:3079–3084, 1991.
Kobayashi et al., "Enzymatic Polymerization: The First in Vitro Synthesis of Cellulose via Nonbiosynthetic Path Catalyzed by Cellulase," *Makromol. Chem., Macromol. Symp.*, 54/55:509–518, 1992.
Kobayashi et al., "Effect of Saccharide Monomer Structure of Enzymatic Polymerization," *Polymer Preprints*, 41:1093, 1992.
Kobayashi et al., "A Novel Method or Cellooligosaccharides Synthesis by using Enzyme Catalyst," *Polymer Preprints*, 41:1094, 1992.
Obata et al., "Enzymatic Synthesis of Novel Oligosaccharides Having Galactose Unit at the End," *Polymer Preprints*, 41:2415–2417, 1992.
Kobayashi et al., "A Novel Method for Synthesis of Cellooligosaccharide Derivatives by Using Emzyme Catalyst," *Chem. Lett.*, 685–686, 1993.
Shoda et al., "Synthesis of New Oligosaccharides by Enzymatic Lactosylation," *The 65th Annual Meeting of the Chemical Society*, Japan, Mar., 1993, Abstracts, p. 613.
Karthaus et al., "Synthesis of Functional Oligosaccharides by Enzymatic Glycosylation," *The 65th Annual Meeting of the Chemical Society, Japan*, Mar., 1993, Abstracts, p. 613.
Kobayashi et al., "Enzymatic Synthesis of Polysaccharides Using α–D–Maltosyl Fluoride," *XVth International Carbohydrate Symposium*, Aug. 12–17, 1990 (Yokohama, Japan), Abstracts, p. 125.
Kobayashi et al., "Enzymatic Polymerization of α–D–Maltosyl Fluoride Utilizing α–Amylase as the Catalyst: A New Approach for the Synthesis of Maltooligosaccharides," *Macromolecules*, 25:3237–3241, 1992.
Shoda et al., "Structure of Substrate Monomer and Its Polymerizability in Enzymatic Polymerization," *Polymer Preprints*, 41:2418–2420, 1992.
Shimada et al., "Synthesis of Unnaturaal Oligosaccharides Using an Enzyme Catalyst," *Polymer Preprints*, 40:3035–3037, 1991.
Shoda et al., "Cellulase–catalyzed, Stereoselective Synthesis of Oligosaccharides," *J. Chem. Soc., Chem. Commun.*, Aug. 31, 1993.
Kobayashi, S., "Success in the Chemical Synthesis of Cellulose," *Chemistry and Industry*, 44:1914–1918, 1991.
Kobayashi and Shoda, "Synthesis of Cellulose and Cellooligosaccharides by Enzymatic Polymerization," *Chemistry and Biology*, 31:385–391, 1993.

(List continued on next page.)

*Primary Examiner*—Marian C. Knode
*Assistant Examiner*—Francisco C. Prosts
*Attorney, Agent, or Firm*—Arnold, White & Durkee

[57] ABSTRACT

The present invention discloses a method of synthesizing a novel form of cellulose I as well as methods of synthesizing a novel form of cellulose I in vitro. One method comprises contacting an activated saccharide substrate with an endoglucanase in an appropriate organic solvent/buffer ratio. The invention also encompasses a partially purified endoglucanase and a method of synthesizing cellooligosaccharides. A second method comprises contacting a nucleotide sugar with a purified glycosyl transferase in an appropriate buffer medium to insure polymerization and crystallization of parallel glucan chains from the enzyme/micelle complex to form cellulose I.

4 Claims, 10 Drawing Sheets

OTHER PUBLICATIONS

Brauns, D. H., "Optical Rotation and Atomic Dimension. VIII. Halogeno–Hepta–Acetyl Derivatives of Melibiose and Maltose. The Structures of Bioses and Cellulose," *J. Am. Chem. Soc.*, 51:1820–1831, 1929.

Brown, R. Malcolm, Jr., "Bacterial Cellulose," *Cellulose: Structural and Functional Aspects*, Ellis Horwood Limited, Publishers, Chapter 16, pp. 145–151, 1989.

Brown, R. Malcolm, Jr., "Cellulose Microfibril Assembly and Orientation: Recent Developments," *J. Cell. Sci. Supp.*, 2:13–32, 1985.

Brown and Montezinos, "Cellulose Microfibrils: Visualization of Biosynthetic and Orienting Complexes in Association with the Plasma Membrane," *Proc. Natl. Acad. Sci. USA*, 73(1):143–147, 1976.

Bureau and Brown, "In Vitro Synthesis of Cellulose II from a Cytoplasmic Membrane Fraction of Acetobacter xylinum," *Proc. Natl. Acad. Sci, USA*, 84:6985–5989, 1987.

Chanzy et al., "Colloidal Gold Labeling of 1,4–β–D–glucan Cellobiohydrolase Adsorbed on Cellulose Substrates," *FEBS Letters*, 172(2):193–197, 1983.

Henrissat et al., "Synergism of Cellulases from Trichoderma Reesei in the Degradation of Cellulose," *Biotechnology*, 3:83–87, 1985.

Delmer, Deborah P., "Cellulose Biosynthesis," *Ann. Rev. Plant Physiol.*, 38:259–290, 1987.

Elbein, A. D., "The Synthesis of Cellulose by an Enzyme System from a Higher Plant," *J. Am. Chem. Soc.*, 86:309–310, 1964.

Fry, Stephen C., "The Growing Plant Cell Wall: Chemical and Metabolic Analysis," *Monographs and Surveys in the Biosciences*, Longman Scientific & Technical, Essex, U.K., publishers, pp. 96–97.

Hayashi et al., "UDP–Glucose: (1→3)–β–Glucan Synthases from Mung Bean and Cotton," *Plant Physiol.*, 83:1054–1062, 1987.

Hirano, Shigehiro, "The Preparation of a Cellulose–like Polymer from 2,3,6–Tri–O–(N–phenylcarbamyl)–D–glucopyranose by the Action of Phosphorus Pentoxide in Dimethyl Sulfoxide," *Agr. Biol. Chem.*, 37(1):187–189, 1973.

Husemann and Kern, "Über die Synthese unverzweigter Polysaccharide," *Die Makromolekulare Chemie*, 91:212–230, 1966.

Itoh and Brown, "The Assembly of Cellulose Microfibrils in Valonia macrophysa Kütz," *Planta*, 160:372–381, 1984.

Kuga, Shigenori, "Native Folded–Chain Cellulose II," *Polymer*, 34(15):3293–3297, 1993.

Kuga and Brown, "Correlation Between Structure and the Biogenic Mechanisms of Cellulose: New Insights Based on Recent Electron Microscopic Findings," *Structure and Biogenic Mechanisms*, pp. 677–688.

Lai et al., "Evidence for a Covalent Intermediate Between α–Glucosidase and Glucose," *Biochemical and Biophysical Research Communications*, 60(2):635–640, 1974.

Lin and Brown, "Purification of Cellulose Synthase from *Acetobacter Xyliunum*," *Cellulose and Wood*, John Wiley & Sons, New York, publishers, pp. 473–492, 1989.

Lin et al., "Synthesis of Fibrils in Vitro by a Solubilized Cellulose Synthase from *Acetobacter xylinum*," *Science*, 230:822–825, 1985.

Lin et al., "Identification of the Uridine 5'–Diphosphoglucose (UDP–Glc) Binding Subunit of Cellulose Synthase in *Acetobacter xylinum* Using the Photoaffinity Probe 5–Azido–UDP–Glc," *J. Biol. Chem.*, 265(9):4782–4784, 1990.

Markwell et al., "A Modification of the Lowry Procedure to Simplify Protein Determination in Membrane and Lipoprotein Samples," *Analytical Biochemistry*, 87:206–210, 1978.

Mayer et al., "Polypeptide Composition of Bacterial Cyclic Diguanylic Acid–Dependent Cellulose Synthase and the Occurrence of Immunologically Crossreacting Proteins in Higher Plants," *Proc. Natl. Acad. Sci. USA*, 88:5472–5476, 1991.

Mueller and Brown, "Evidence for an Intramembrane Component Associated with a Cellulose Microfibril–Synthesizing Complex in Higher Plants," *J. Cell Biology*, 84:315–326, 1980.

Nakatsubo et al., "Toward the Synthesis of Cellulose: Synthesis of Cellooligosaccharides," Chapter 24, Part 3, pp. 201–206.

Rānby, Bengt G., "The Mercerisation of Cellulose," *Acta Chemica Scandinavica*, 6:101–115, 1952.

Roelofsen, P. A., "Cell–Wall Structure as Related to Surface Growth," *Aca Botanica Neerlandica*, 7:77–89, 1958.

Ross et al., "Regulation of Cellulose Synthesis in Acetobacter xylinum by Cyclic Diguanylic Acid," *Nature*, 325:279–281, 1987.

Sarko, Anatole, "What is the Crystalline Structure of Cellulose?" *Tappi*, 61(2):59–61, 1978.

Saxena et al., "Identification of a New Gene in an Operon for Cellulose Biosynthesis in *Acetobacter xylinum*," *Plant Molecular Biology*, 16:947–954, 1991.

Saxena et al., "Cloning and Sequencing of the Cellulose Synthase Catalytic Subunit Gene of *Acetobacter xylinum*," *Plant Molecular Biology*, 15:673–683, 1990.

Schuerch, C., "The Chemical Synthesis and Properties of Polysaccharides of Biomedical Interest," *Advances in Polymer Science*, Springer–Verlag, Publishers, pp. 173–194, 1972.

Sekiguchi and Takagi, "Ultrastructure of Nucleoli in Oocytes of *Patella coerulea*," *Nature*, 183:1136–1137, 1959.

Sisson, Wayne A., "The Existence of Mercerized Cellulose and its Orientation in Halicystis as Indicated by X–ray Diffraction Analysis," *Science*, 87:350, 1938.

Updegraff, David M., "Semimicro Determination of Cellulose in Biological Materials," *Analytical Biochemistry*, 32:420–424, 1969.

Uryu et al., "Ring–Opening Polymerization of 1,4–Anhydro–2,3,6–tri–O–benzyl–α–D–glucopyranose and 1,4–Anhydro–2,3,6–tri–O–D–galactopyranose," *Macromolecules*, 18:599–605, 1985.

Wong et al., "Genetic Organization of the Cellulose Synthase Operon in *Acetobacter xylinum*," *Proc. Natl. Acad. Sci. USA*, 87:8130–8134, 1990.

Wood and Bhat, "Methods for Measuring Cellulase Activities," *Methods in Enzymology*, 160:87–107, 1988.

FIG. 2A
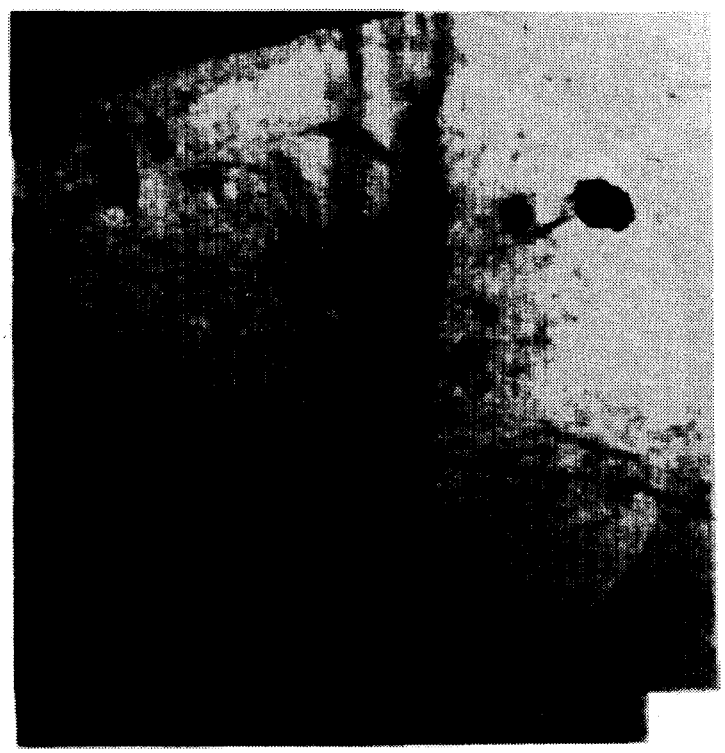
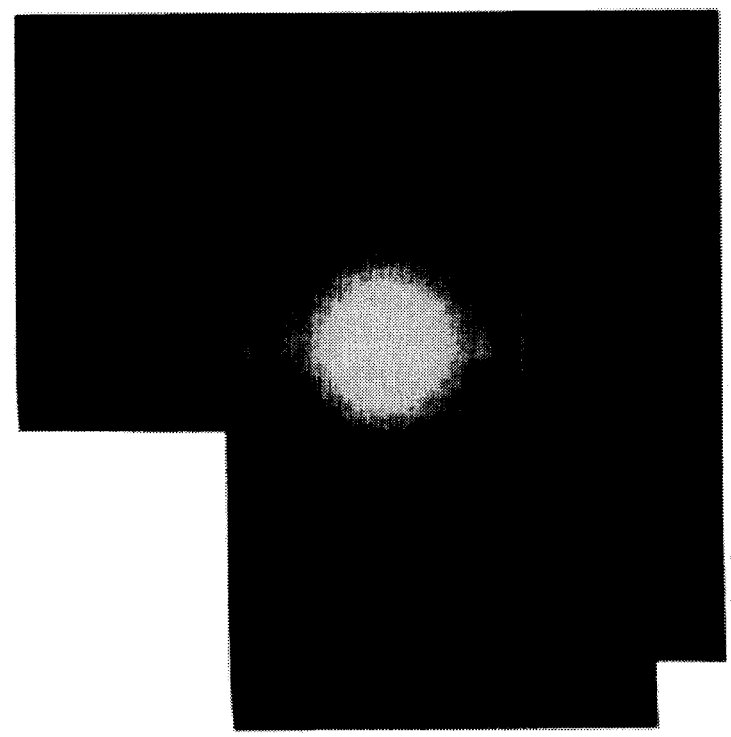
FIG. 2B

FIG. 2C
FIG. 2D

ENZYMATIC METHOD FOR SYNTHESIS OF CELLULOSE 1

BACKGROUND OF THE INVENTION

1. Field of the Invention

The present invention relates generally to the in vitro production of polysaccharides, cellooligosaccharides and more particularly to the synthetic production of a novel form of cellulose I.

3. Description of the Related Art

Cellulose is the most abundant macromolecule on earth (Brown, 1985). It serves a major structural role in the cell wall of plants, some algae, and certain fungi and is the primary component of economically important products such as wood, cotton, and paper. Because of its tremendous abundance and its physiological and economic importance, many attempts at in vitro cellulose synthesis have been made with cell-free systems from various sources during the past three decades (Delmer, 1987; Brown, 1989b; Read and Delmer, 1991). The greatest progress has been made using Acetobacter xylinum as an experimental model (Ross et al., 1987; Brown, 1989a; Lin and Brown, 1989; Lin et al., 1990; Saxena et al., 1990; Wong et al., 1990; Mayer et al., 1991; Saxena et al., 1991). However, until very recently (Okuda et al, 1993) no preparation from higher plant cells has ever been shown to be capable of synthesizing true microfibrillar cellulose or even appreciable quantities of β-1,4-glucan (Read and Delmer, 1991). In the present inventors previous work a considerable progress was made over earlier research of in vitro cellulose synthesis (Okuda et al, 1993). Although not yet approaching cellulose synthesis rates in vivo the present inventors have clearly detected a cellulose product synthesized in vitro.

The methods for synthesizing cellulose in vitro are as follows. The plasma membrane from cotton fibers is extracted with 50 mM Tris-HCl buffer (pH 7.5), containing 5 nM EGTA, 20% PEG and combination of protease inhibitors. The resulting plasma membrane fraction is solubilized in 10 nM Tris-HCl (pH 7,4), containing 1% digitonin, 1 mM EDTA, 1 mM EGTA, 10% glycerol. The in vitro product is synthesized under conditions favoring β-1,4-glucan synthesis. The resulting in vitro product is characterized by solubility, enzymatic digestion, degree of polymerization (DP) determination, methylation linkage analysis, x-ray diffraction and transmission electron microscopy (TEM) coupled with autoradiography and CBHI-gold labeling. Although the product synthesized by this method is cellulose, it is cellulose II. Thus, until the present invention described herein, there has been no method known to synthesize the cellulose I polymorph in vitro from higher plant extracts.

Native cellulose predominantly occurs as a fibrillar crystalline allomorph designated cellulose I. Cellulose I consists of a crystalline array of glucan chains, all of which are oriented parallel to one another (Preston, 1974). Cellulose I can be transformed to the more stable allomorph, cellulose II, via chemical treatments that alter the crystal structure (Rånby, 1952; Sarko, 1976). This change is strictly irreversible, and no process has been known that gives cellulose I either by recrystallization or by polymerization in vitro. Cellulose II recently has been found to have a folded chain, antiparallel conformation (Kuga, et al, 1993). It has been argued that cellulose I is thermodynamically metastable and, therefore, that living organisms control crystallization in a manner not duplicated under acellular conditions (Rånby, 1952; Sarko, 1976; Blackwell, 1982; Sawyer and George, 1982).

Native celluloses exist in a polymorphic form known as cellulose I or crystalline polymorphs thereof (Preston, 1974). This polymorph is known to contain glucan chains that are parallel to each other. The cellulose I polymorph is characteristic of almost all native celluloses synthesized by living systems to date. Cellulose II is only rarely synthesized under natural conditions. Halicystis (an alga) (Rånby, 1952; Sisson, 1938; Roberts, 1991), Sarcina (a bacterium) (Roberts, 1991; Roelfsen, 1959) and a mutant strain of Acetobacter xylinum (a bacterium) that produces folded-chain cellulose II (Kuga et al., 1993) are the few known organisms producing native cellulose II. Cellulose I is a metastable polymorph; it exists in a more thermodynamically unstable form than that of the cellulose II polymorph. In this form, the glucan chains are antiparallel to one another, and there is one additional hydrogen bond linking each glucose residue. Cellulose II is formed when cellulose I is dissolved and reprecipitated.

Electron diffraction analysis has shown that native celluloses are synthesized in a crystalline form. The electron diffraction patterns are characteristic for each type of cellulose polymorph or allomorph (both words are used interchangeably in this invention). That is, cellulose I is a polymorph that has characteristic electron diffraction patterns different from those of cellulose II. At the ultrastructural level, the crystalline form of cellulose can be visualized by a variety of electron microscope techniques, among them negative staining. This technique is useful in that it can identify small aggregates of glucan chains down to a mean diameter of approximately 12–15 Å.

In vitro synthesis of cellulose has been one of the most difficult, yet important and challenging topics of the early stages of macromolecular science. Much effort has been devoted to regio- and stereoselective preparations of cellulose, i.e., construction of stereoregular polysaccharides having β-1,4 glycosidic linkages. The chemical approaches so far attempted, however, have failed to solve the problem in spite of the remarkable development of modern synthetic methods (Klar, 1963; Husemann, et al., 1966; Hirano, 1973; Schuerch, 1972; Uryu, et al., 1985).

In one attempt, the condensation of 2,3,6-glucose tricarbanilate with phosphorus pentoxide in a mixture of chloroform/dimethyl sulfoxide gave branched products, however, the molecular weight of the resulting polysaccharide after removing the protecting group was low (Husemann, 1966). In a Lewis acid catalyzed reaction, 1,4-Anhydro-2,3,6-tri-O-benzyl-a-D-glucose has been polymerized giving rise to polymers having mixed structures of β-1,4 (cellulose-type) and α-1,4 (amylose-type) linkages. Uryu and coworkers investigated the possibility of synthesizing polysaccharides having β-1,4 linkages (cellulose) by the cationic ring-opening polymerization of 1,4-anhydroglucose derivatives. However, stereoregular polysaccharides having the desired structure were not obtained due to the lack of regioselective ring opening (Uryu, et al., 1985).

Concerning a stepwise synthesis of cellooligosaccharide derivatives, several oligomers up to an octamer have been synthesized starting from allyl 2,3,6-tri-O-benzyl-4-O-(p-methoxybenzyl)-β-D-glucoside; however, elimination of the protecting groups from a specific oligomer, e.g., cellooctaose, has not been achieved (Nakatsubo, 1989). The in vitro synthesis of cellulose utilizing biosynthetic pathways has been reported exploiting *Acetobacter xylinum* (Colvin, 1959) or *Phaseolus aureus* extracts (Elbein, 1964) with a nucleoside diphosphate sugar (ADP, CDP, or GDP-glucose) as the substrate.

Two of the present inventors have reported a different approach for the synthesis of cellulose, i.e., by a transglycosylation reaction (condensation polymerization) catalyzed by cellulase, an extracellular cellulose hydrolytic enzyme, with β-D-cellobiosyl fluoride as a glycosyl donor (Kobayashi, et al., 1991). β-D-cellobiosyl fluoride was chosen as the activated glycosyl donor because a disaccharide is the smallest molecule recognized by the enzyme. The configuration of the C1 fluorine atom of the starting material was designed to form a reactive intermediate leading to a β-1,4 product (cellulose) via a "double displacement mechanism" (Lai, 1974) at the active site of the enzyme. The major advantage of this approach was that it did not involve protection and deprotection of the hydroxyl groups. Several organic solvents/buffers were investigated with an acetonitrile/acetate buffer being the most preferred, and a 5:1 ratio was found to be the best ratio for the production of cellulose. Although cellulose was produced by this method, the product was cellulose II. So, unfortunately, there was still no in vitro method to synthesize the more useful cellulose I polymorph. In European Patent Specification application No. 87307891.9 (Brown et al., 1987) in vitro cellulose synthesis was reported. However such cellulose was not synthesized but created only after washing a synthesized product with strong base or other solubilizing agents to remove contaminants.

The present invention overcomes these and other drawbacks inherent in the prior art by providing a method of producing cellulose I either synthetically by a non-biological reaction, or by using a biological catalyst in vitro.

SUMMARY OF THE INVENTION

One method of the present invention for synthetic cellulose assembly involves reacting an activated saccharide moiety with a partially purified cellulolytic enzyme in a medium of an appropriate organic solvent/buffer ratio. The method for biologically driven cellulose I assembly in vitro involves a nucleotide sugar and a micellar organized array of cellulose synthases in an aqueous environment.

The activated saccharide moiety may be any substrate which is a monosaccharide, disaccharide, oligosaccharide, polysaccharide or combinations thereof. For example, a preferred substrate is a disaccharide. However, a monosaccharide or a monosaccharide joined by a glycosidic bond to another saccharide moiety having substrate activity is usable. Other possible substrates include glycoproteins, glycolipids and oligosaccharides. The particularly preferred activating group on the saccharide substrate is an agent, such as a fluoride atom chemically bonded to the reducing end of the saccharide (Brauns, 1929). Other preferred activating groups are generally halogens, halogen derivatives such as iodide, methyl, allyl, trifluoroethyl and acetyl. The activating group is also in the desired anomeric configuration to yield the desired anomeric glycosidic bond.

The enzyme to be used in the method of the present invention may be a glycosyltransferase, an endoglucanase, a hydrolase or a cellulolytic enzyme and the hydrolyase may be used in combination with one or more glycosyltransferases. For synthetic cellulose I assembly, preferably, a cellulolytic enzyme is allowed to react with an activated cellobiosyl substrate under conditions favoring the reverse reaction, resulting in the formation of new glycosidic bonds rather than their hydrolysis. A preferred enzyme is a partially purified from Onazuka R-10 Cellulase. Cellulase Onazuka R-10 (Kinki Yakult, Osaka, Japan), "Onazuka Cellulase" is a commercial preparation of crude cellulases from Trichoderma viride containing several dozen polypeptides. For biologically driven cellulose I assembly in vitro, a purified glycosyltransferase is allowed to react with the nucleotide sugar, UDP-glucose under conditions favorable for cellulose (over callose) and under conditions more specifically favorable for the in vitro synthesis of the cellulose I polymorph.

The present invention comprises a method of producing synthetic cellulose I which involves contacting an activated disaccharide monomer with a partially purified cellulolytic enzyme immobilized by containment in micelles or affixation to a solid matrix. A preferred disaccharide is activated by a bound halogen atom, methyl, allyl, trifluoroethyl, or acetyl. The preferred halogen is fluorine.

The preferred cellulolytic enzyme is a partially purified fraction of Trichoderma viride cellulase and more preferably is a P-100 or a P-60 fraction of Trichoderma viride cellulase that contains endoglucanases. A more preferred enzyme preparation has an at least a 31 fold increase in specific activity from a Trichoderma viride crude cellulase preparation. Most preferably the enzyme is a 39 kDa polypeptide consisting of more than 90% of a partially purified Trichoderma viride cellulase fraction.

The preferred micelles comprise substrate dissolved in an aqueous buffer and an organic solvent. The organic solvent is preferably ethanol, methanol, acetone, 1,4-dioxane, nitromethane, N,N-dimethylformamide, dimethyl sulfoxide, isooctane, or propionitrile. A most preferred organic solvent is acetonitrile. The micelles are preferably formed in an organic solvent/aqueous buffer with a ratio between 5:1 and 2:1. Most preferably the micelles are formed at a 5:1 acetonitrile: aqueous buffer ratio and by varying substrate concentrations. Cellulose I is preferably synthesized by varying the substrate concentration from 5 mg/reaction to 4 mg/reaction and with micelles that are formed in an organic solvent/aqueous buffer ratio of 2:1.

An important aspect of the present invention is an at least partially purified cellulolytic enzyme preparation capable of synthesizing cellulose I from an activated disaccharide substrate. This is preferably an at least partially purified fraction of cellulase from Trichoderma viride. In an aspect, the enzyme or enzyme preparation comprises at least one partially purified cellulolytic enzyme capable of synthesizing cellulose I from an activated disaccharide substrate.

The present invention also comprises a method of synthesizing cellooligosaccharides, said method comprising contacting an activated disaccharide monomeric substrate with an at least partially purified enzyme preparation or a combination of specific enzyme preparations, from Trichoderma viride wherein said enzyme or preparation of enzymes comprise at least one endoglucanase. In an important embodiment, this enzyme or enzyme preparation preferably comprises at least one endoglucanase and at least one glycosyltransferase.

The most preferred activated disaccharide substrate is cellobiosyl fluoride. The present invention additionally involves synthetic cellulose I obtained by the methods described herein. This cellulose I preferably consists essentially of β-glucan sheets comprising no more than two layers of glucan chains in thickness.

The method of cellulose I synthesis of the present invention comprises biopolymerization of glucose with aid of an ordered biocatalyst to form individual glucan chains; wherein hydrophobic interaction between said glucan chains results in formation of single glucan chain sheets and said glucan chain sheets are stacked to form a crystalline cellulose I allomorph.

The ordered biocatalyst is, in one embodiment, an enzyme complex whose subunits are organized in a rosette or linear arrangement. This ordered biocatalyst is under genetic control of a living system through conventional DNA/RNA/protein synthesizing pathways leading to specific conformations to affect the specific arrangement of subunits. The hydrophobic interactions and stacking may be realized but to different degrees, leading to cellulose I morphologies not synthesized by living systems.

The present invention, in one aspect, involves specific arrangement of enzymes in the micelle is usually controlled by at least one of a ratio between organic solvent and aqueous buffer, a concentration of activated disaccharide substrate and substrate polarity. When the activated disaccharide is a cellobiosylfluoride, it has a hydrophobic fluorine group and a hydrophilic cellobiose moiety. It is important, in certain embodiments, that micelle size and arrangement of components within said micelle insure parallel glucan chain extrusion in a unidirectional manner to form crystalline cellulose I allomorph.

The crystalline cellulose I allomorph consists of two glucan chain sheets in thickness but consists of 5 or more glucan chains within said glucan chain sheets. A novel thin form of cellulose I is due to specific organization or lack thereof of the synthetic micelle complex which controls glucan sheet stacking to form the crystalline allomorph. The solid matrix to which cellulose-synthesizing enzymes are attached may be a fiber or a colloidal gold particle. A preferred fiber is a nitrocellulose fiber, or a proteinaceous fiber. The biocatalyst of the present invention may be cellulose synthase, although it may be a glycosyl transferase. A combination of glycosyl transferases, particularly in combination with a biocatalytic cellulose-synthesizing system, may be used to form an oligosaccharide.

The P-100 and P-60 enzyme fractions described herein are partially purified preparations from the crude Onazuka R-10 Cellulase. Partial purification of the cellulase has been achieved through a combination of gel permeation chromatography, preparative isoelectric focusing, salting out, and preparative electrophoresis. These steps have led to the partial purification and identification of a single 39 kDa polypeptide which appears to be responsible for synthetic cellulose production.

The "P-100" Fraction

An initial attempt to identify and isolate the factor/s from the *Trichoderma viride* cellulase system that are responsible for synthesizing cellulose resulted in a partially purified preparation denoted as "P-100" based on the use of a P-100 gel filtration column as the ultimate step in the purification scheme. The P-100 fraction was found to contain about 8 polypeptide bands representing major polypeptides, and minor polypeptides appearing as smears in the region between about 66 kDa and 35 kDa on the sodium dodecylsulfate polyacryamide gel (SDS-PAGE). Cellulase activity was determined by quantifying water-insoluble synthetic cellulose yields of each collected fraction throughout the purification procedure. The P-100 fraction exhibited a 10 fold increase in synthetic activity over the crude enzyme. Protein concentrations were determined using a modification of the Lowry procedure (Markwell, 1978). A flow chart for obtaining the P-100 fraction is shown in FIG. 5.

The "P-60" Fraction

It was not possible to identify which of the 8 or more proteins in the P-100 fraction was responsible for synthesizing cellulose; therefore, an ammonium sulfate fractionation was added to the purification regime. Furthermore, the P-100 column was changed to a P-60 column in order to achieve better separation. The most active fraction collected from the P-60 gel purification also appeared to contain about 8 polypeptides when analyzed on an SDS-PAGE gel, however, there was one major polypeptide band at 39 kDa. This 39 kDa polypeptide comprised about 80% of the total protein of the most active fraction, while in comparison, the P-100 fraction did not contain any single polypeptide band that was more concentrated than the others. There was a 31-fold increase in synthetic activity from the crude enzyme to the most active P-60 fraction. A cellulytic activity assay (Wood, 1988) using carboxymethylcellulose and Avicel as substrates indicated that the P-60 fraction contained endoglucanase activity, but cellobiohydrolase activity was lacking. FIG. 6 is a flow chart for the purification of the P-60 enzyme fraction.

There has also been a further purification of the P-60 enzyme fraction achieved by preparative electrophoresis. More than 90% of this newly purified fraction from the Prep Cell-preparative electrophoresis was the 39 kDa polypeptide and there were 2 or 3 very minor bands. This fraction also produced synthetic cellulose I. This is further evidence that the 39 kDa protein is the enzyme responsible for synthetic cellulose. This band is related to other endoglucanases by the criteria used in the literature to define endoglucanases. The criteria are based on the ability of the hydrolase to completely degrade carboxymethyl cellulose, but with a very low activity toward crystalline cellulose. The endoglucanases have a random cleavage pattern, in contrast to the exoglucanases (e.g. cellobiohydrolase I) which systematically attacks from the non-reducing end to cleave out cellobiose.

Synthetic cellulose was also produced with cellulase preparations from other sources, *A. niger, P. tulipiterae*, and *P. chrysaspi*, for example. Preliminary results have also been obtained indicating that all endoglucanases are active in synthesizing cellulose. The P-60 fraction that contains the 39 kDa polypeptide has the highest endoglucanase activity and also has the highest cellulose synthesis activity. But so far, endoglucanase I and II from *T. viride* and endoglucanase from *P. chrysaspi* also have good synthetic activity (cellulose I). It appears to be important that the normally cellulolytic enzyme usable for cellulose synthesis be purified to the point that enzymes having cellulolytic activity without synthetic activity under the reaction conditions for cellulose synthesis are effectively excluded from the enzyme preparation. For example, particularly exoglucanases as well as those endoglucanases which have low synthetic activity are preferably removed, thereby leaving only the endoglucanase(s) with high cellulose synthetic activity. Low synthetic activity endoglucanases may concomitantly have high hydrolytic activity. The net reaction should be shifted towards synthesis as much as possible in the immobilization such as system of micelles with aqueous buffer and organic solvent. It is contemplated that these undesired hydrolases, if present at undesired levels, would compete with the polymerization reaction by hydrolyzing the product at a rate that precludes the desired glucan chain polymerization in the synthesis of cellulose I or other products. An indication that all endoglucanases are active to some extent in synthesizing cellulose comes not from the different sources of cellulase listed above but from specifically testing 3 different endoglucanases, e.g. endoglucanase I and endoglucanase II, both from *T. viride,* and an endoglucanase from *P. chryaspi*. From these data, it appears that all endoglucanases to an extent can probably synthesize cellulose under the conditions described herein. This suggests a common mechanism for the reaction but it does not explain why one specific endoglucanase (our 39 kDa polypeptide) has much greater activity than any other endoglucanase thus far found.

It is quite novel and unexpected that an endoglucanase would be the enzyme involved to polymerize cellobiosylfluoride. At first thought the cellobiohydrolase I or CBH I exoglucanase would have been believed to be the logical synthetic candidate since it has the inherent ability to cleave out cellobiose. So the endoglucanase-related discovery of the present invention is further clarified as completely unexpected.

The concentration of the synthetic enzymes is also an important aspect in the method of the present invention, as the packing, or orientation of the enzymes in the micelles appears to depend on the concentration of enzyme. The proper packing, or orientation of the catalytic sites of the enzymes, then directs the proper crystallization of cellulose I. Of course, it is understood that different solvent/buffer combinations or substrate concentration may form different sized micelles and that the important embodiment of the present invention is the formation of correctly oriented enzymes in a micelle for example, and that any variation in enzyme concentration that is able to synthesize cellulose I is encompassed within the scope of the present invention.

It is understood that many possible solvents may be used within one method of the present invention. These solvents include, but are not limited to ethanol, methanol, acetone, 1,4-dioxane, nitromethane, N,N-dimethylformamide (DMF), dimethyl sulfoxide (DMSO) isooctane and propionitrile. The organic solvent may be necessary for the ordering of the enzyme complexes as discussed above. The organic solvent/aqueous buffer ratio should be within a range that allows some separation of organic and aqueous environments dispersed throughout the solution, such as micelles, and yet does not produce a complete biphasic separation.

It is recognized that each organic solvent/buffer combination will require a different ratio in order to achieve maximum efficiency of the reaction. These ratios may also be adjusted in order to achieve the desired products, for example different polymer lengths and different crystallization patterns may be achieved by adjusting the solvent/buffer ratios. A preferred solvent for the production of cellulose I is acetonitrile in a solvent/buffer ratio of from about 2:1 to about 5:1 and most preferably about 2:1. With only a reasonable amount of experimentation, for example with different solvents and/or different solvent ratios, one skilled in the art could follow cellulose I production and arrive at optimal synthetic conditions.

A certain embodiment of the present invention is that the highly polar substrate, cellobiosylfluoride can have a marked effect on the nature of micelle formation. It is understood that each different ratio will require different concentration of cellobiosylfluoride. For example, even under a 5:1 solvent ratio condition, by adjusting the concentration of substrate, macrobiphasic separation can be prevented.

A certain embodiment of the present invention is a purified cellulolytic enzyme capable of producing synthetic cellulose I by utilizing an activated saccharide substrate. Said cellulolytic enzyme, in a most preferred aspect, can be further defined as a 39 kDa endoglucanase derived from a partially purified fraction of Onazuka Cellulase R-10. This enzyme can be even further defined as part of the P-100 or the P-60 fraction of said Onazuka Cellulase R-10. It is understood, however, that other endoglucanases from Onazuka R-10 and other cellulases can also produce synthetic cellulose.

As mentioned above, although preferred for use in certain embodiments, there is no general requirement that the cellulolytic enzyme always be provided in its most purified state. Indeed, it is contemplated that less substantially purified enzymes, which are nonetheless enriched in certain cellulolytic activity relative to the natural state, will have utility in certain embodiments. These include, for example, the production of cellooligosaccharides and alternate crystallization states of cellulose and other glucan polymers. Partially purified cellulase fractions for use in such embodiments may be obtained by subjecting a crude extract to one or a combination of the steps described above.

It will be appreciated that once the cellulolytic enzyme is purified, it can be sequenced and/or replicated by techniques well-known to those skilled in the art. For example, replication might be accomplished by recombinant techniques involving the isolation of genetic material coding for the cellulolytic enzyme and the preparation of an immortal cell line capable of producing the cellulolytic enzyme. The cellulolytic enzyme, once the gene is cloned, can be overexpressed in for example, an *E. coli* strain and can be modified, for example by site directed mutagenesis. It is understood that the use of such modified enzymes is within the scope of the present invention.

The present invention also encompasses a method of synthesizing cellooligosaccharides. Control of the molecular weight of the cellooligosaccharide polymers may be accomplished by simultaneously adjusting the organic solvent/buffer ratios and by using different enzyme preparations. For example, by adjusting the organic solvent/buffer ratio and the purity of the enzyme preparation, i.e. the presence of competing hydrolases, one may control the degree of polymerization (D.P.) of the product. Such controls may include changes in temperature, reaction time, increased scale, etc.

The molecular weight of the polymers synthesized by the method of the present invention might also be controlled by mechanical agitation of an immobilized catalytic complex. After determination of the rate of synthesis in each in vitro system, the mechanical agitation or periodic ultrasonic bursts could be programmed to reach the desired molecular weight.

It is also understood that by the use of alternate activated substrates, specific polysaccharides could be synthesized. Other saccharide substrates that could be used include, but are not limited to glucose, galactose, arabinose, xylose, rhamnose, etc. or oligosaccharides thereof as analogs of the preferred cellobiosyl fluoride. This method would include the use of other hydrolases, endoglucanases as well as glycosyltransferases such as xylosyltransferase, e.g., that are specific for the desired glycosidic bonds and could include one or more endoglucanases and/or one or more glycosyltransferases. The substrates mentioned above may also be used in an activated form and as such would be included within the scope of the present invention. A specific hydrolase may be used for a specific substrate, xylanase for xylan, mannosidase for mannans, galactosidase for galactose, etc.

A certain embodiment of the present invention is a new and novel composition of synthetic cellulose I which is obtainable by the method described in the present disclosure. This composition can be further defined as a crystalline isomorph of cellulose I wherein said cellulose I is comprised of β-glucan sheets, said β-glucan sheets being no more than two layers of glucan chains in thickness. All known naturally occurring cellulose I crystals are at least 3 chains thick resulting in electron diffraction patterns that are distinguishable from the data obtained with the cellulose I synthesized with the method of the present invention. Morphological studies of the synthetic cellulose indicate crystal dimensions of 12 Å×25 Å, a dimension never found in nature. It is also contemplated that cellulose I fibrils with a larger degree of polymerization than found in nature are possible in light of the present disclosure. DP. of 23,000 may be the upper limit from native cellulose I (Kuga et al., 1989). It is understood that these long polymers would also be encompassed by the present invention.

The present invention also comprises a method which give in vitro cellulose I assembly from cotton extracts. This method applies improved buffer systems and double solubilization steps. For isolation of plasma membrane 50 nM 3-{N-morpholino propanesulfonic acid (MOPS), (pH 7.5), containing 5 nM EDTA and 0.25M sucrose was used. A solubilized enzyme fraction was obtained by a two-step digitonin solubilization. In the first step, the plasma membrane was treated for a short time with first solubilization buffer, containing 50 nM MOPS (pH 7.5) 0.25M sucrose and 0.05% digitonin. In the second solubilization step the resulting pellet was treated with 50 nM MOPS (pH 7.5), containing 0.25% sucrose and 1% digitonin. The product was synthesized using combined first and second solubilized enzymes under the condition favoring β-1.4-glucan synthesis (Okuda et al, 1993). Most of the resulting product had the morphology of cellulose I and a small amount of cellulose II and was strongly bounded with CBHI-gold particles. Obtained in this way the in vitro product was in the form of true microfibrils with diameter of 8–26 Å. It should be emphasized that the cellulose I microfibrils synthesized in vitro do not have the same size as the cellulose I synthesized in vivo, where, the microfibrils are 35–40 Å in diameter. Thus, using a natural biosynthetic pathway enzyme system, we have achieved cellulose I assembly for the first time, but with a novel form of the polymorph. The major advantage of this approach for in vitro cellulose I synthesis was applying a different buffer systems and a double solubilization steps.

Cellulose, the main component of wood, paper, cotton, rayon and other yarns is one of the world's most important polymers. The ability to synthesize synthetic cellulose is thus an extremely important invention which has been sought by researchers over many years. The ability to synthesize new forms of cellulose also creates the possibility of the creation of stronger, denser, or even lighter fibers than those that occur in nature. Therefore, this invention answers a long felt and important need in many fields of materials research and utility.

BRIEF DESCRIPTION OF THE DRAWINGS

FIG. 1A depicts cellulose synthesized in 5:1 acetonitrile/acetate buffer, showing mostly non-fibrillar cellulose II, with occasional bundles of long fibrils. Both forms are strongly labeled with colloidal gold-cellobiohydrolase I, a specific marker of cellulose.

FIG. 1B shows cellulose produced in an acetonitrile/buffer ratio of 2:1. Under these conditions, the production of fibrillar material was significantly enhanced.

FIG. 1C depicts cellulose II and cellulose I synthesized in a 5:1 organic solvent/buffer ratio.(mag=122,000×).

FIG. 1D shows cellulose I at high magnification (=92,000×) which was produced in a 2:1 organic solvent/buffer ratio.

FIG. 2A, FIG. 2B, FIG. 2C and FIG. 2D depict the results of electron diffraction studies of synthetic cellulose from P-100 and P-60 fractions.

FIG. 2A is a more highly magnified (mag=76,000×) electron micrograph of the fibrillar cellulose produced in a 2:1 acetonitrile/acetate buffer ratio with the P-100 fraction.

FIG. 2B is the electron diffraction pattern of the product in 2A.

FIG. 2C. Cellulose I product from the P-60 enzyme fraction under 2:1 acetonitrile/aqueous buffer ratio.

FIG. 2D. P-60 fraction 2:1 acetonitrile/aqueous buffer ratio, cellulose I electron diffraction pattern. Note the absence of the 6.0 Å reflection which is expected from the two glucan chain sheet layer.

FIG. 3 depicts conditions favoring cellulose II synthesis (with the 5:1 acetonitrile/aqueous buffer ratio). Note that with this ratio and 5 mg of substrate, the reaction mixture undergoes a macroscopic phase separation.

FIG. 4 depicts conditions favoring cellulose I (with the 2:1 acetonitrile/aqueous buffer ratio). Note that with this ratio and 5 mg of substrate, the reaction mixture does not undergo a macroscopic phase separation.

DETAILED DESCRIPTION OF THE PREFERRED EMBODIMENTS

An important embodiment of the present invention is the in vitro synthesis of cellulose I by several different methods and using various concentrations of different catalysts and different substrates. These will be outlined below. This list does not limit the scope of the invention, nor does it imply that these are the only substrates, catalysts or physical methods possible to assemble cellulose I. It is important however, to select an appropriate catalyst, suitably purified, and an appropriate substrate. Then it is important to make certain that the glucan chains are polymerized in such close proximity to one another that they have no room to collapse or fold on each other. Under these conditions, the glucan chains will spontaneously and irreversibly form parallel glucan chain aggregates which can further associate with other glucan chain aggregates to form larger parallel glucan chain clusters having the crystallinity typical of the cellulose I allomorph. The parallel chain orientation insures higher molecular weight polymers and concomitantly longer fibrils.

An embodiment of the present invention is the synthesis of cellulose I via an enzymatic polymerization of cellobiosyl fluoride, catalyzed by a partially purified cellulase preparation in an optimized organic solvent/aqueous buffer system and concentration of substrate. The production of microfibrillar cellulose I in this system appears to be the result of a micellar aggregation of the synthesis-active components, a condition that promotes fasciation of the glucan chains with the same polarities and extended chain conformations.

In vitro cellulose synthesis by cellulose synthetase from the natural monomer, uridine diphosphate glucose, always has resulted in the formation of cellulose II (Lin et al., 1985; Bureau and Brown, 1984; Okuda et al., 1993). Until now, the synthesis of cellulose by the reaction involving a cellobiosyl fluoride substrate, crude cellulase, and an organic solvent system also have led to the formation only of cellulose II in the form of irregular rodlets (Kobayashi et al., 1991). Cellulose II is nonfibrillar, while all known forms of cellulose I have a fibrillar morphology.

The unique characteristics of cellulose I and its predominance in nature relate to the fact that an extended chain conformation confers mechanical strength as well as flexibility through fibrillar forms. With this arrangement, cellulose molecules can aggregate and crystallize into submicroscopic reinforcing rods known as microfibrils. The arrangement and orientation of cellulose microfibrils within the cell wall control the growth expansion axis and give the plant tissue the strength necessary for survival in turbulent environments.

Figure 8A:
FIG. 8A shows the fibrillar in vitro product strongly labeled with CBHI-gold particles without negative staining.
Figure 8B:
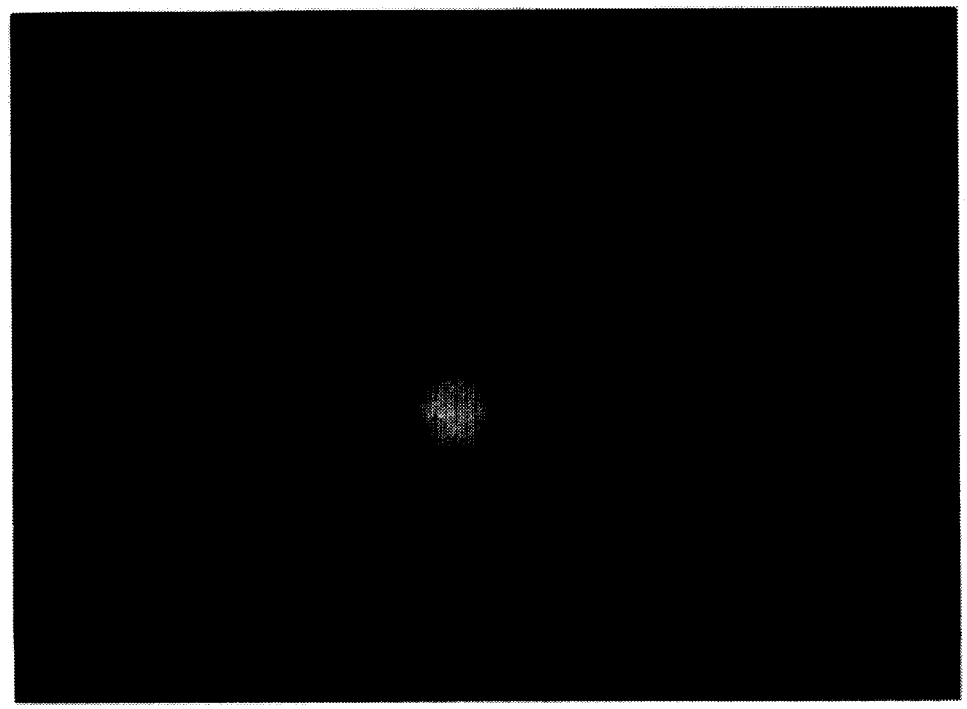
FIG. 8B depicts the result of electron diffraction pattern of the same in vitro product shown in 8A with a typical reflections for cellulose I and the gold particles.
Figure 9:
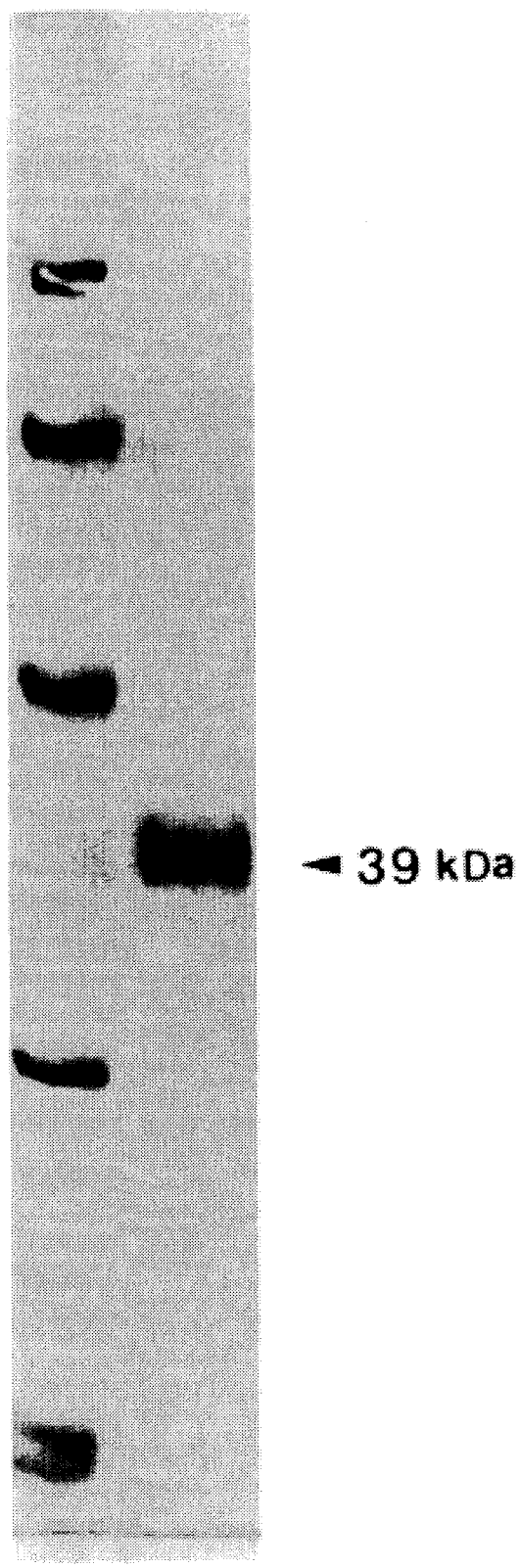
FIG. 9 is a SDS-PAGE gel showing the final purification fraction from a Prep Cell™. Note the prominent 39 kDa band with very minor bands below it. 39 kDa is the polypeptide that is responsible for synthetic cellulose activity.

Cellulose I is one of nature's most orderly biopolymers. Thus, it is of great interest to duplicate this perfection in non-living systems. In the method of chemical synthesis cited in Kobayashi et al. 1991, cellobiosyl fluoride is polymerized through catalysis by Onazuka R-10 Cellulase in an acetonitrile/buffer ratio of 5:1. The reverse of the normal hydrolysis reaction is attained by the combination of an environment of reduced water activity and the fluorinated monomer which has a strong inclination to polymerize. The Onazuka Cellulase is a commercial preparation of crude cellulases from *Trichoderma viride* containing at least several dozen polypeptides. In an attempt to isolate the enzyme/s responsible for the reaction, a partially purified preparation (denoted here as the P-100 fraction) was obtained. This partially purified fraction contains 8 major polypeptide bands by sodium dodecylsulfate-polyacrylamide gel electrophoresis (SDS-PAGE). In a further purification, a fraction denoted as P-60 was obtained which contains a major 39 kDa protein with several minor proteins when visualized on SDS-PAGE (FIG. 8).

Figure 1B:
FIG. 1A, FIG. 1B, FIG. 1C and FIG. 1D include transmission electron micrographs of cellulose synthesized by partially purified cellulase (P-100 fraction) with cellobiosyl fluoride as substrate.
Figure 1D:
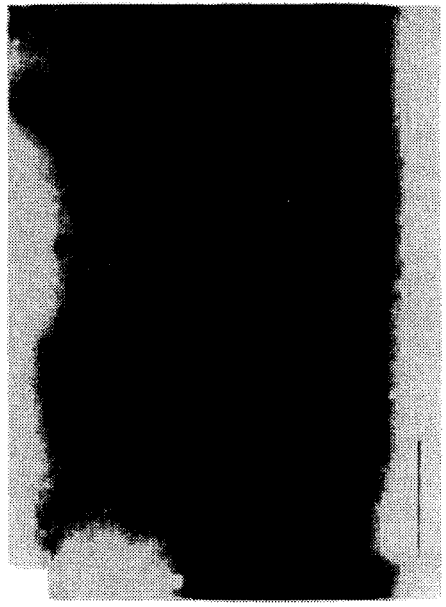
Figure 1A:
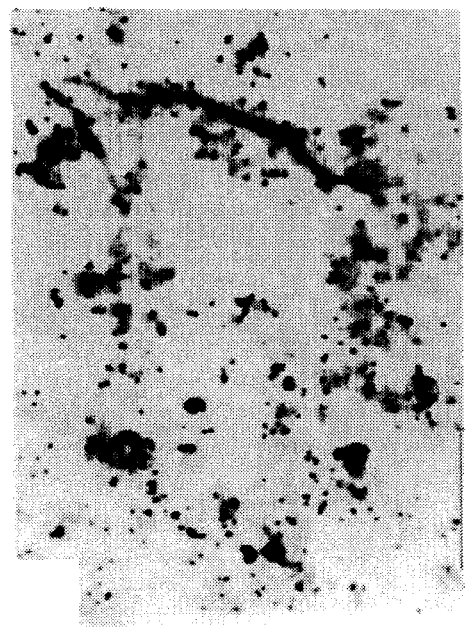
Figure 1C:

When testing the partially purified P-100 fraction for cellulose synthesizing activity, it was found that the product contained fibrillar materials dispersed randomly among rodlets. These fibrils were similar to those of cellulose I formed in vivo, and could be labeled with a specific cellulose probe, colloidal gold-cellobiohydrolase (FIG. 1A).

To enhance the production of the fibrillar material, various conditions were studied, especially the acetonitrile/buffer ratio. An enhanced cellulose synthesis was attained by an optimal ratio of 2:1 acetonitrile/buffer. Under these conditions, large aggregates of fibrillar material were synthesized (FIG. 1B). This permitted an electron diffraction analysis of the fibrils, which clearly indicated a cellulose I pattern combined with a cellulose II pattern (FIG. 2A) from the rodlets in the surrounding area (FIG. 2B).

To eliminate the possibility that the observed fibrils might be contaminants, various controls were performed, including one control which lacked substrate. Fibrils or rodlets were never found during the incubations without substrate, indicating that the observed fibrils are the enzymatic reaction products.

A time-course of the reaction was visualized with electron microscopy. The P-100 enzyme fraction, when dissolved in acetate buffer, yielded particles of about 4 nm in diameter, which are believed to be individual enzyme molecules with some larger aggregates of enzyme molecules. When the P-100 fraction was introduced into the acetonitrile/buffer (2:1), distinct micellar aggregates of proteins were observed. Thirty seconds after addition of cellobiosyl fluoride to this mixture, short disorganized fibrils were seen emanating from a depression within an aggregated complex. At 3 min. incubation, the extended fibrils became elongated and more organized. Continued incubation up to 20 minutes resulted in larger and longer fibrillar aggregates. Because of excessive aggregation, the product needed intense ultrasonic treatment to produce fibrils thin enough for electron microscopic observations (FIG. 1B).

During the past 16 years since the discovery in freeze fractured membranes of presumptive organized cellulose synthesizing complexes known as terminal complexes or TCs (Brown & Montezinos, 1976) the literature is replete with examples of organized TCs from bacteria (Brown & Montezinos, 1976) algae (Brown & Montezinos, 1976), (Itoh & Brown, 1984), (Brown, 1985) and vascular plants (Mueller & Brown, 1980). Thus, the synthesis of cellulose I in nature appears to require an organized array of catalytic subunits in order to assemble parallel glucan chains unidirectionally. As a result of cellulose synthesis, these TCs move in the plane of the fluid membrane (in the case of plant cells), or push forward the cellulose microfibrils into the environment (in the case of extracellular secretion by bacteria).

Synthesis of cellulose I in the present system indicates that the conditions of the present invention have reproduced some of the natural conditions under which this allomorph is produced. The microscopic phase separation in this system, i.e., the micellar aggregation of enzyme molecules appears to have mimicked the organized structure of the natural cellulose I synthesizing system.

Figure 3:
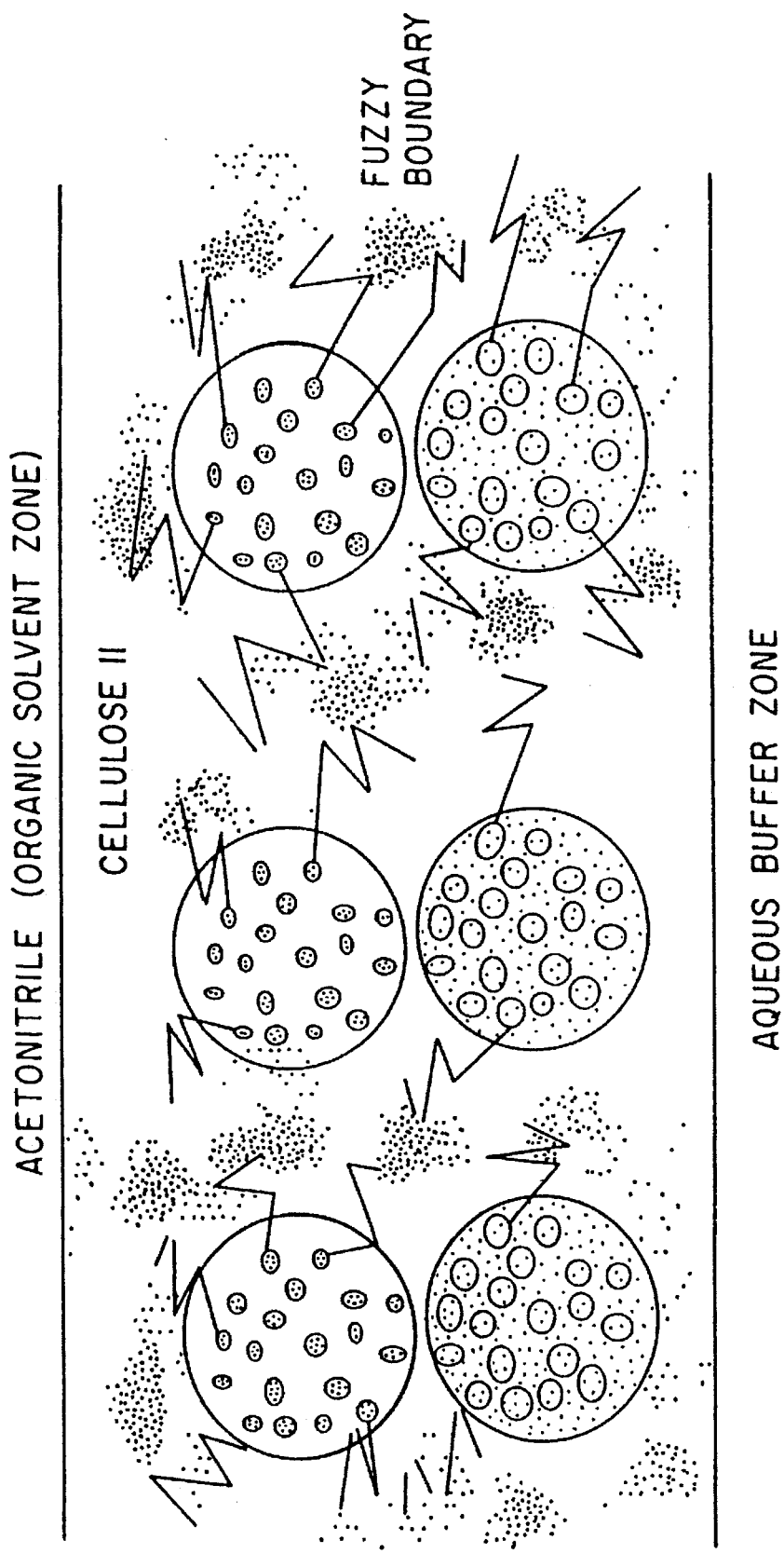
FIG. 3 and FIG. 4 are schematic diagrams depicting the two conditions leading to the predominant synthetic assembly of cellulose I or cellulose II.

Because of the poor solubility of the enzyme and the substrate in acetonitrile/buffer, the reaction mixture undergoes a complex phase separation at the initial stage. With an acetonitrile/buffer ratio of 5:1 and 5 mg of substrate, the reaction mixture immediately undergoes a macroscopic phase separation resulting in the formation of a single, separated layer (FIG. 3), with most of the reaction product formed at the interface between the aqueous and hydrophobic phases. The product under these conditions is mostly cellulose II rodlets and barely detectable quantities of cellulose I.

Figure 4:
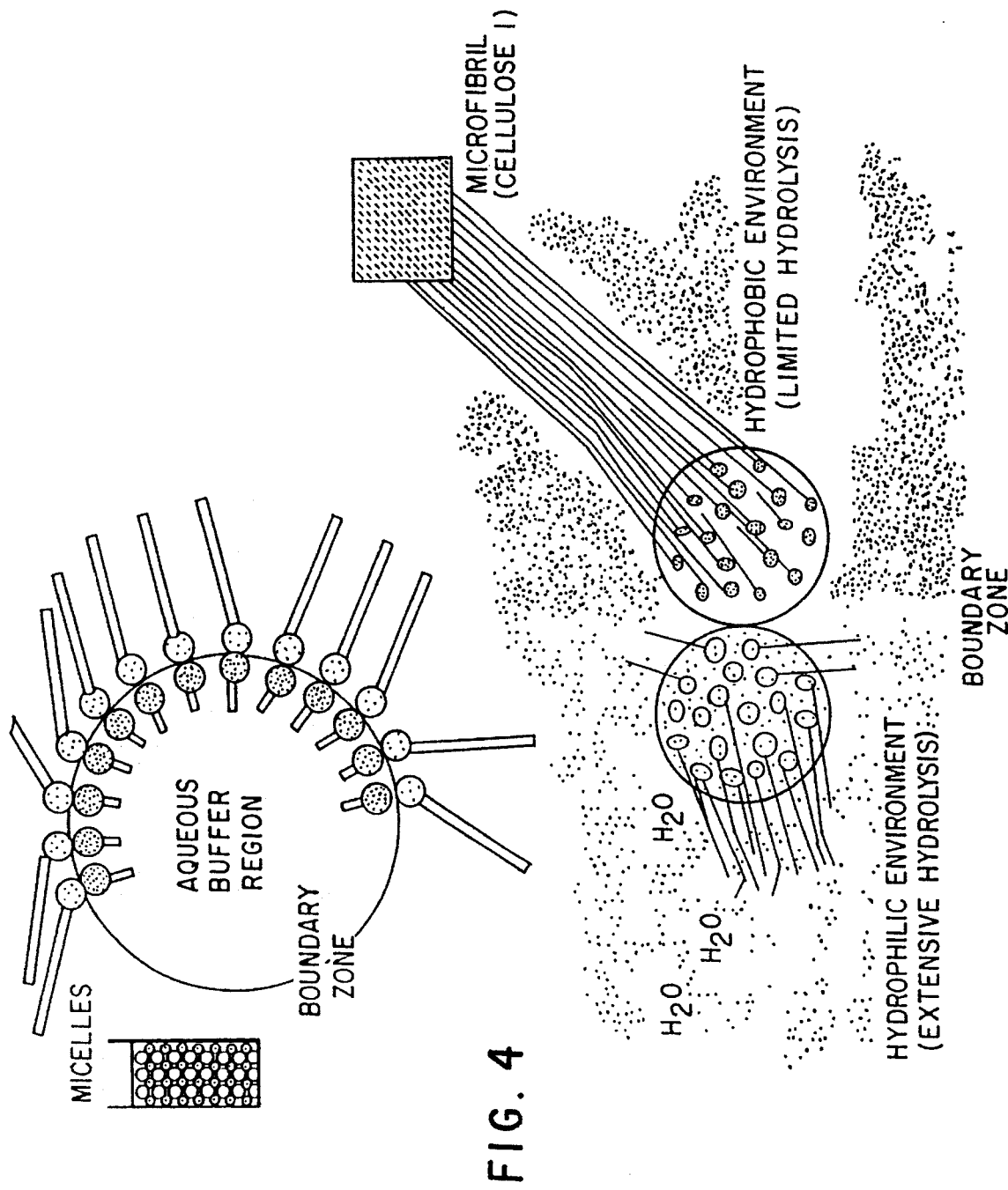

However, with an acetonitrile/buffer ratio of 2:1 and 5 mg of substrate, no distinct phase boundary is formed; instead, the entire solution becomes turbid upon the addition of substrate (FIG. 4). The resulting microscopic micelles which formed were visualized by electron microscopy (FIG. 3B). Under these conditions the P-100 enzyme fraction produced an enhanced amount of cellulose I, while the crude enzyme produced cellulose II only.

A surprising discovery of the present invention is that the combination of the partially purified enzyme preparation and the lower acetonitrile to buffer ratio allows the glucan chains to grow simultaneously and unidirectionally into an extended chain conformation, achieving an artificial terminal complex.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

Synthetic Cellulose I Assembly

The 5:1 acetonitrile/acetate buffer reaction mixture was prepared as described elsewhere (Kobayashi, 1991). The 2:1 acetonitrile/buffer reaction mixture was prepared by dissolving 50 mg of the P-100 fraction (See Example II, infra) in 0.05M sodium acetate buffer (pH 5) to give a total volume of 0.032 ml. Five milligrams of substrate was dissolved in 0.064 ml of the same buffer and 0.192 ml of acetonitrile. Reactions were run at room temperature (25° C.) for 20 min. The reaction product was repeatedly washed with water at 4° C., and subjected to 30 seconds of ultrasonication with a Fisher Dismembrator-Model 300.

For electron microscopy, the samples were mounted on copper grids coated with thin carbon films, negatively stained with a 2% uranyl acetate containing 0.01% bacitracin (except for the electron diffraction specimens), and examined with a Philips 420 TEM operating at 100 KV or 120 KV (Kobayashi et al., 1993). For the time-course study, a drop of the control solution or the reaction mixture was directly placed on the grid, excess solution was removed and the preparation was dried.

When the acetonitrile/buffer ratio was adjusted to 2:1 and the concentration of the P-100 enzyme fraction was 50 micrograms, keeping the substrate, cellobiosyl fluoride at 5 milligrams, huge fibers of cellulose I were produced. The fibers were abundant in the entire EM grid. The bundle width was up to 1 mm, and the individual microfibrils within the bundle were in very close alignment with each other. Individual microfibrils were approximately 12 Å×25 Å. CBH I-Gold sparingly labeled these microfibrils, indicating that there were relatively few non reducing ends for labeling.

As seen in FIG. 2B, the cellulose I pattern is intermixed with the cellulose II pattern. However, when the enzyme fraction is changed from the P-100 to the P-60 fraction, surprisingly, the cellulose II is almost non-existent (FIG. 2D). The cellulose I pattern appears alone with some of the cellulose II pattern appearing at other areas of the grid. This indicates that by increasing the purity of the enzyme and by preventing phase separation, the micelles are further saturated, thus achieving a denser multiple array of catalytic sites for parallel extended glucan chain formation.

EXAMPLE II

Purification of Cellulolytic Activity

It is a surprising embodiment of the present invention that with a partially purified cellulase, cellulose I is synthesized under conditions that only produce cellulose II when crude cellulase preparations are used. The inventors studies, based on numerous trials, indicate that a substantial degree of catalyst purification is required before cellulose I can be synthesized in vitro using cellulase as the catalyst. It is believed that the purification must be such as to remove the enzyme activity which hydrolyses the cellulose I in competition with the desired reverse cellulose synthesis reaction. It is also contemplated that the purer enzyme preparation may allow more orderly packing of the enzymes in the micelles, thus producing the more ordered cellulose I product.

Purification Method

Figure 5:
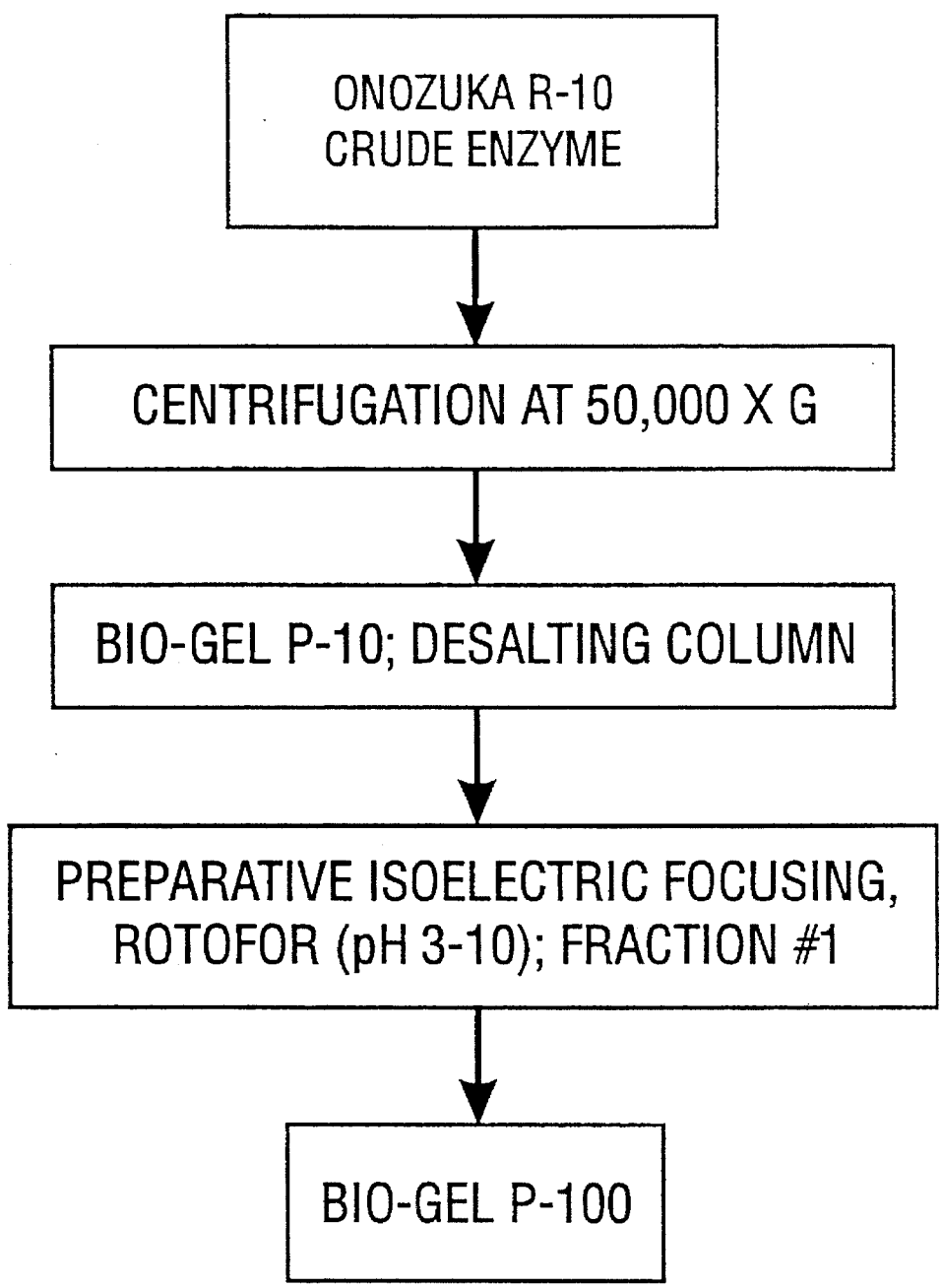
FIG. 5 is a flow chart for generating the P-100 fraction.

Cellulase Onazuka R-10 (Kinki Yakult, Osaka, Japan) was dissolved in 0.01M sodium acetate buffer (pH 5), and insoluble material was removed by centrifugation at 50,000×g. Fifteen milliliters of a 13.3% solution of this preparation was loaded into a Bio-Gel P-10 column (30×500 mm) and the void fraction was collected. Using an Amicon ultracel with a PM 30 membrane, the fraction was concentrated into 10 ml. To 42.4 ml of deionized water and 10 ml of concentrated enzyme solution were added 2.6 ml of a 40% w/v Bio-Lite ampholyte blend (pH 3–10). This mixture was loaded into a Rotofor™ Preparative Isoelectric Focusing Cell (Bio-Rad, California) operating at 12 W constant power for 4 h at 1° C. Twenty fractions of about 2.5 ml each were collected and assayed for cellulose synthesizing activity by measuring the water insoluble product using the anthrone reagent (Fry, 1988). The fraction (pH 3.6) with the highest activity was collected and further purified over a Bio-Gel P-100 column (20×900 mm). The majority of the activity was associated with the shoulder fraction of only one peak. This fraction was used in this study and described as the P-100 fraction. An SDS-PAGE analysis of the P-100 fraction revealed eight broad bands with some evidence of minor bands. See FIG. 5 for the purification scheme.

Figure 6:
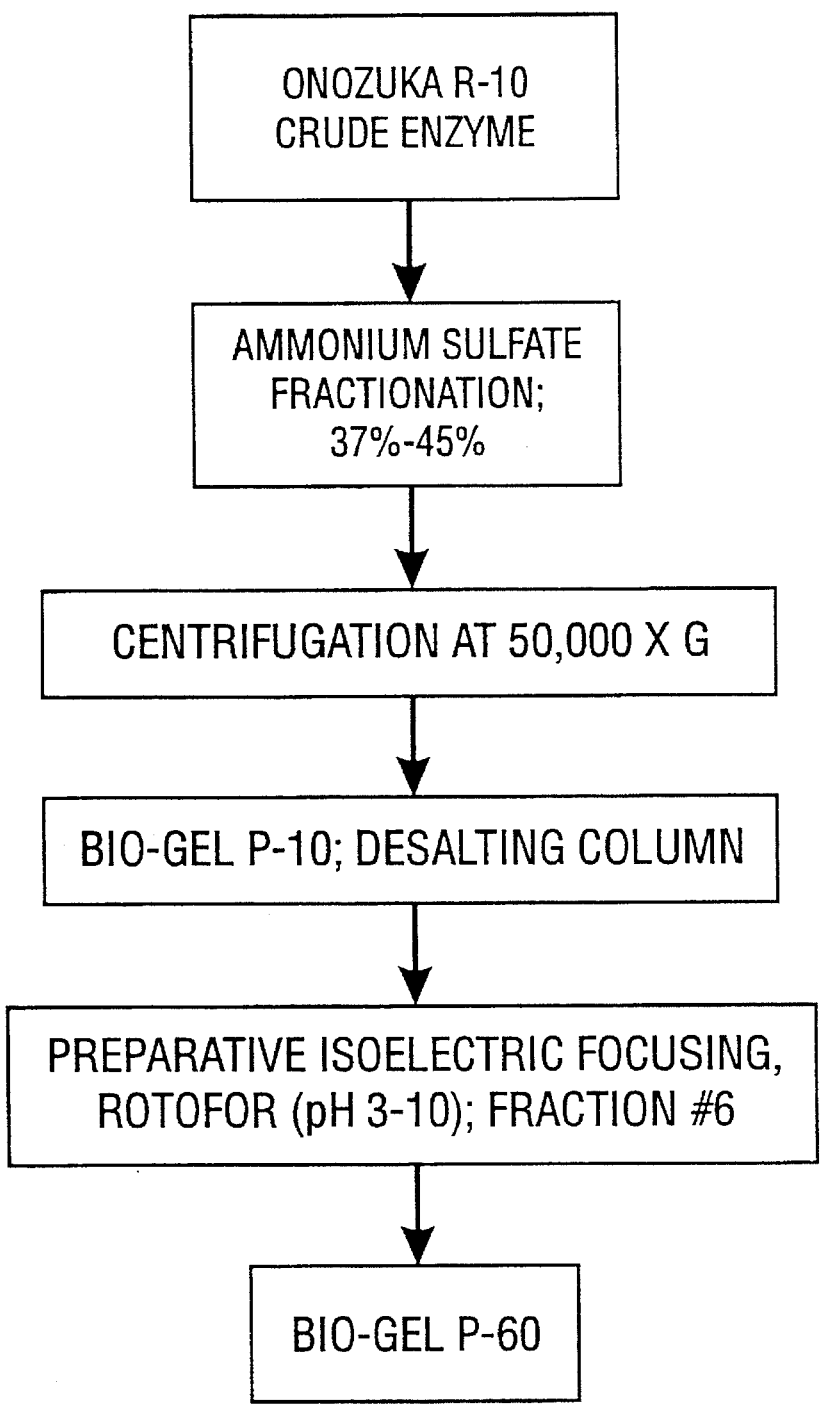
FIG. 6 is a flow chart for generating the P-60 fraction.
Figure 7:
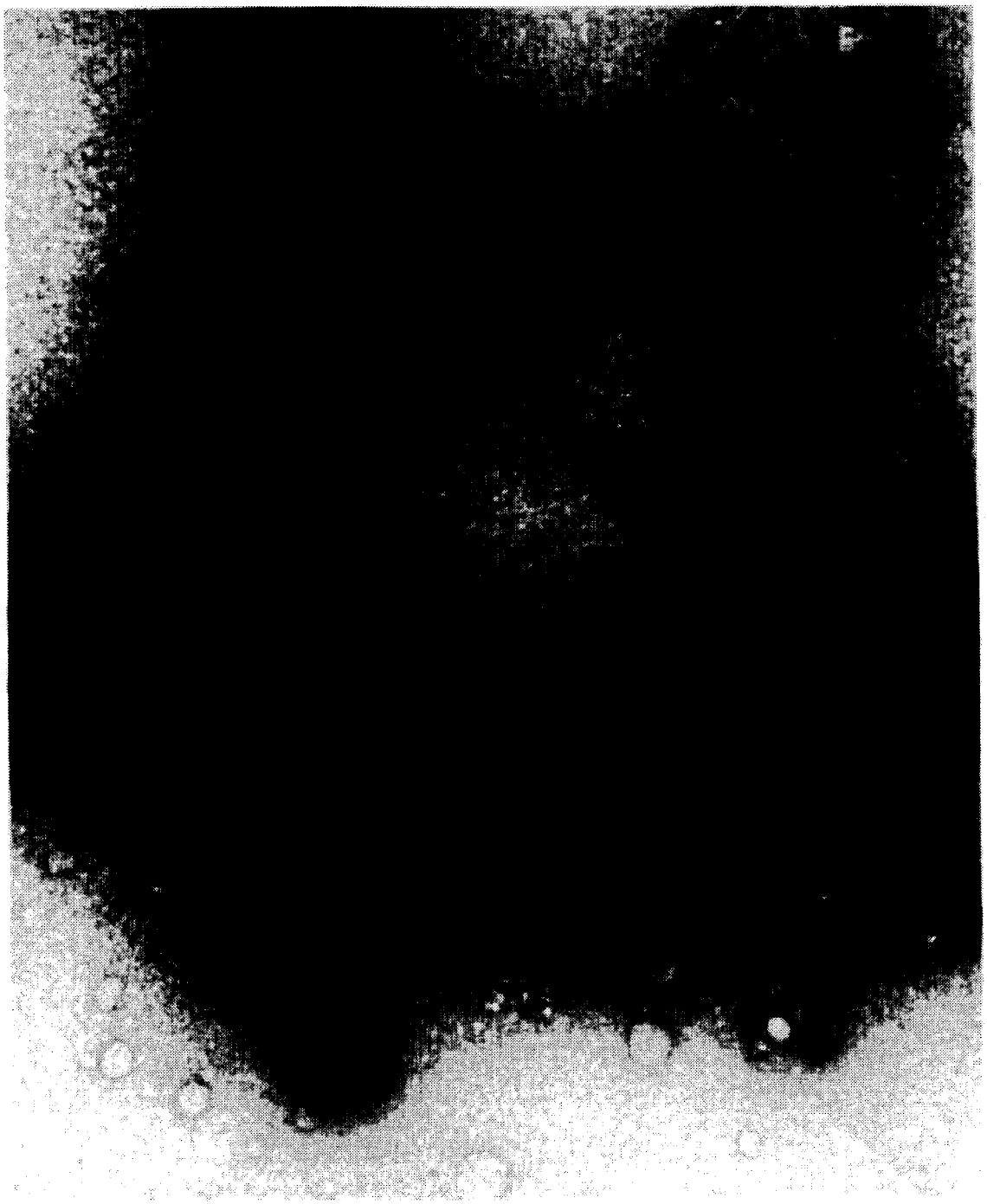
FIG. 7 is the electron micrograph of the fibrillar cellulose I produced in vitro from the cotton extract. The in vitro product was labeled with CBH I-gold complex and negatively stained. (mag=150,000×).

In a further purification, an ammonium sulfate fractionation step was added and the P-100 column was replaced by a P-60 column (FIG. 6). The SDS-PAGE of the product of this purification step revealed a major band at 39 kDa comprising about 80% of the total protein. When a Prep Cell™ (Bio-Rad, Calif.) was employed the 39 kDa protein was >90% of the total protein and there were only 2 or 3 minor bands (FIG. 8). This fraction exhibited a 31-fold higher specific activity than the crude extract and lacked any cellobiohydrolase activity (Wood et al.,

EXAMPLE III

Enzymes Other Than Cellulase

Enzymes other than cellulase are encompassed by the present invention. Preliminary studies have been done with different endoglucanases, cellobiohydrolase I, β-glucosidase and particularly cellobiohydrolase II. Others which may be used in the present invention include, but are not limited to hydrolases such as chitinase, β-1,3 glucanase, β-1,2 glucanase, or xylanase to synthesize, mannosidase to synthesize mannans, or other appropriate candidates. This invention would also include the use of any of the glycosyl transferases already discovered to function in cellulose assembly in Acetobacter, Dictyostelium, Saprolegnia, or cotton, for example.

For natural cellulose synthase systems which use UDP-glucose as the substrate, it is known that in order to generate cellulose I, an organized subunit structure (the TC) must be present. It is contemplated by the present inventors that the subunits may become disorganized during the purification procedures. But under appropriate conditions, such as the conditions of the present invention, the enzymes may be brought into such close proximity as to effect the synthesis of cellulose I in vitro. Therefore, the cellulose synthase enzymes are also encompassed within the scope of the present invention.

EXAMPLE IV

Other Substrates for Cellulolytic Enzymes

In certain embodiments of the present invention, other oligosaccharides such as cellotetrasylflouride, cellopentasylfluoride, etc. could serve as substrates for the cellulase enzyme. The invention would also encompass substrates with active groups other than fluorine, including, but not limited to iodide, methyl, allyl, trifluoroethyl and acetyl groups. In general, the organic solvent would be water miscible up to a certain point, but should not be too highly dipolar aprotic which will cause inactivation of the enzyme. Since it is envisioned that cellulose synthases may be used in the method of the present invention, cellobiose or possibly even glucose could also be used as substrates.

The effect of the monomer structure on the polymerization was investigated using various cellobiose derivatives. a-D-Cellobiosyl fluoride, whose fluorine atom at the anomeric position has the opposite (a) configuration did not polymerize. This result shows that the anomeric stereochemistry plays an important role in this enzymatic polymerization. Other cellobiose derivatives, alkyl cellobioside and 1-O-acylcellobiose derivatives were found to be recognized by the cellulose catalyst. However, these cellobiose derivatives showed poor polymerizability in comparison with that of $\beta$-D-cellobiosyl fluoride under the conditions tested. It is understood that specific conditions may be necessary for each particular substrate/enzyme combination and that these conditions can be determined without undue experimentation in light of the present disclosure. For xylan and mannan synthesis, it is expected that activated monomer derivatives such as xylobiosylfluoride or mannobiosylfluoride can be used.

EXAMPLE V

The Use of Other Solvents

Other possible solvents may include, but are not limited to ethanol, methanol, acetone, 1,4-dioxane, nitromethane, N,N-dimethylformamide (DMF), dimethyl sulfoxide (DMSO), isooctane, and propionitrile. In general, the organic solvent should be water miscible up to a certain point, but should not be too highly dipolar aprotic which may cause inactivation of the enzyme.

Since it has been demonstrated by the inventors that the crystalline structure of the product as well as the degree of polymerization are dependent on the packing of the enzyme complex, it is contemplated that different structural arrangements of the enzymes in the catalytic complexes will result in different products. Therefore, in light of the present disclosure, the organic solvent/buffer combinations can be varied to produce unique crystallization patterns and polymer lengths.

EXAMPLE VI

Synthesis of Cellooligosaccharides

Control of the molecular weight of the cellooligosaccharide polymers may also be accomplished by simultaneously adjusting the organic solvent/buffer ratios, concentration of substrate, and by using different enzyme preparations. For example, more cellulose II is synthesized with a 5:1 organic solvent/buffer ratio with crude enzyme and more cellulose I is produced with a 2:1 organic solvent/buffer ratio and pure enzyme.

The molecular weight of the polymers synthesized by the method of the present invention might also be controlled by mechanical agitation of an immobilized catalytic complex. For example, during normal cellulose biosynthesis in Acetobacter, approximately $10^8$ glucose molecules are incorporated into cellulose/cell/hr. The linear extrusion rate is 2 or more microns/min. This means that it would take 0.12 seconds to produce an cellooligosaccharide with a degree of polymerization (dp) of 8. Thus, an interval of mechanical disruption could be programmed to match the desired molecular weight. The timing of the disruption would have to take into account the hysteresis effect and time delays for re-initiation of synthesis which occur in living cells and cellulose assembly, but which may be reduced during the synthetic reaction. The in vitro rate of synthesis can be determined without undue experimentation.

Polymers produced in this way could be useful for example, for artificial lignification of a cellulose backbone and its branches to synthesize new composite materials with useful mechanical properties and increased strength. Also, lipids could be added to the carbohydrate structure to improve penetration into membranes for drug delivery or to make some new mayonaise-like compounds which have the mouth feel of butter but without the calories. The synthesis of cellooligosaccharides with a dp of 3 or higher would also be an embodiment of the present example.

EXAMPLE VII

Immobilization of the Enzymes

In order for a cellulose I allomorph to be assembled in vitro, the cellulose polymerization catalytic sites from several enzymes must be brought into close proximity. One way this might be accomplished would be by careful extraction of native cellulose synthase complexes so that the multimeric organization of the catalytic sites remains relatively undisturbed.

Alternatively, either the enzyme complex must be immobilized, or it must be free and unrestricted so as to be able to move away from its product and have access to incoming substrate. This is exemplified in natural systems by the enzyme complexes, known as terminal complexes or TCs which have been visualized in cell membranes using the freeze fracture technique. In this natural system, the enzyme complex is always associated with the terminus of the cellulose microfibril it is assembling. The TC is free to move in the plane of the fluid membrane, thus continually moving away from its product.

In past attempts at in vitro cellulose synthesis, the enzyme complex, if intact, has been disrupted and separated from the membrane. As the catalysis proceeds, the enzyme complex becomes entrapped within its product, and eventually the reaction slows or stops altogether. This is because the product cannot be moved away from the catalytic site resulting in product inhibition or possibly conditions favorable to the reverse reaction through mass action.

Thus, immobilization of the enzyme complex in such a way that the product could be extruded away from the catalytic complex would permit, on an industrial scale, the continuous generation of polymers. The interface formation and/or micellar formation of the present invention is favorable for the in vitro assembly of cellulose since it is an intrinsically dependable method for separation of the substrate/catalyst/product during the reaction. For example, the enzyme complex is held in the micelle and the product is extruded into the aqueous medium.

The immobilization of the many catalysts on or within a micelle promotes the crystallization of many polymer chains. The degree of order of the enzymes determines the ultimate chain packing, either parallel or antiparallel. During micelle formation, it is important that enzyme or catalyst immobilization takes place for the directed synthesis of glucan chains to form cellulose I. If the isolated catalytic subunits were merely solubilized in suspension, they would create free β-1,4-glucan chains which would then collapse into the more thermodynamically stable folded chain cellulose II crystalline structure.

Fibers as an immobilisation substrate

Immobilization of purified cellulolytic enzymes allows the nascent cellulose product to move away from the enzyme while the reaction proceeds in a hydrophilic environment. For example, since proteins bind to nitrocellulose, a nitrocellulose fiber could be used to immobilize the endoglucanase. Also, any fiber, either natural or synthetic which has a high affinity for binding proteins or which can be modified to chemically bind the catalyst without loss of activity, is a good candidate for the immobilization.

A specific cross linking agent could be glutaraldehyde or another bifunctional agent which would not damage the catalytic site. A protein fiber (hair, silk, collagen, etc.) would be a preferred choice as an immobilization substrate because the efficiency of cellulose production could be monitored by using a dye such as Tinopal which binds to the cellulose product and which can be monitored through its fluorescence.

Optimal reaction conditions for the immobilized enzyme reaction would be established empirically without undue experimentation. Variables would include various combinations of acetonitrile/buffer ratios and temperatures as well as substrate concentration, etc. Other variables include fiber orientation to optimize substrate flow and accessibility to the catalytic sites as well as the product removal downstream. One important consequence of the immobilized enzyme for cellulose synthesis is that the hydrolysis can be minimized or prevented as long as the product continually is removed from the catalytic sites.

Immobilization in a cylindrical chamber

It is envisioned that cellulose can be assembled continuously or intermittently using a confined cylindrical structure within which is placed a membrane which immobilizes the catalyst/s and one which also is permeable to the substrate. As the fluid carrying the substrates plus activators passes through the membrane, these components come in association with the catalyst whereupon the substrates are converted into the growing polymer. The polymer is directed away from the catalyst by the fluid flow. The polymer chains being directed away also are in parallel association with each other so that when they crystallize, the cellulose I allomorph is made. The idea is unique in that to develop such a functional system will require a precise method for bringing the catalytic enzymes, cellulose synthases or cellulases or others into close proximity so that the glucan chains do not get entangled and thus entrap the catalyst. If this happens, the reaction will auto-terminate. As long as the substrate is provided in excess and as long as the product is continuously removed from the catalyst, the reactions will proceed smoothly.

It is important to note that the enzymes must be positioned on the membrane in such a way that they are organized on an approximately spherical surface (=micelle-like component). This can be accomplished possibly by using an organic solvent with the water solvent, adjusting the ratio of solvents or varying the concentration of substrate so that a very fine spherical droplet suspension with the enzymes on the surface is produced. The hydrophobic and hydrophilic groups on the enzyme will determine the nature and degree of positioning of enzymes on the droplet surface at the interface of the micelle.

The glucan polymer chains initially grow in an unrestricted manner in all directions. As the growing chains come into contact with their nearest neighbors, this contact establishes the directionality of collapse, thus leading all the other glucan chains growing from the surface to adhere and bond with the elongating crystalline microfibril or sub-microfibril or glucan chain aggregate. Implicit in this invention is the idea that the size of the spherical surface area can contribute specifically to the structural characteristics of the cellulose I allomorph produced. For example, a large microfibril might be produced if many different spherical droplets with their enzymes were sufficiently closely packed, hexagonally for example, so that the glucan chain aggregates themselves would unite and bond and crystallize with their nearest neighbors. The result of this hierarchical assembly is that the crystalline structure would literally "grow" thus possibly achieving the largest crystals of cellulose ever made. Theoretically, the highly crystalline structure could be as large as several microns or even approach the dimensions of individual yarns such as cotton fibers, or polyester fibers.

Colloidal Gold

It is also contemplated that the endoglucanase or catalyst may exhibit bifunctionality. For example, if the catalyst is a glycoprotein, the carbohydrate moiety may serve to hold the product in the organic solvent micelle phase during the synthesis of cellulose I. This may serve to orient the glucan chains in positions favorable for the metastable crystallization to form cellulose I.

Extending this bifunctionality, the carbohydrate groups on the enzyme may effect the observed high frequency of clumping of enzymes upon activation in the aqueous phase. Adding colloidal gold and electrostatically binding the gold to the enzyme favors clumping. This should initiate an excellent immobilization platform for the enzyme complex to generate cellulose I. The gold would be in the center of the complex binding the endoglucanases by their carbohydrate tails and the polypeptide catalytic heads would be positioned to the surface. This would make a TC for generating parallel glucan chains. Since the gold is dense, the gold enzyme complex could be loaded in an organic phase and by gravity, would descend through the fluid during synthesis, thus producing oriented cellulose. The evidence that this might work is based on data that CBH-gold complexes still retain their cellulose binding activity as well as their catalytic activity (Chanzy et al., 1984).

This concept is not limited to simple physical clumping of the colloidal gold. The colloidal gold could be specifically deposited into many known geometrical arrangements (rows, arcs, cones, triangles, etc.) to provide specific geometric sites for subsequent binding with endoglucanase or the catalytic component. Thus synthetic TCs could be made to organize glucan chains to assemble cellulose microfibrils with specific shapes, sizes, and crystalline perfection.

EXAMPLE IX

New Forms of Cellulose

One isomorph of the cellulose I synthesized by the method of the present invention appears to be a new form not seen in nature. The synthetic cellulose fibril appears to be composed of only two glucan chain sheets and the closest natural cellulose from Vaucheria (Mizuta, et al., 1989) and Erythrocladia (Okuda, et al., personal communication) has at least 3 layers per sheet.

Many types of new synthetic celluloses may be made by this invention. Cellulose with extremely high molecular weight could possibly be produced with a molecular weight of 10 million or more. This has never been achieved by natural living systems or by in vitro systems. The inventors anticipate many different crystalline microfibril shapes to be made by this invention. Square or rectangular cross sections, or even almost membrane-like sheets of cellulose I could be made. The synthesis of these sheets could be controlled by varying the ratio of organic solvent to buffer since it is known that in a 5:1 acetonitrile/aqueous buffer, mostly cellulose II is produced, while in a 2:1 acetonitrile/aqueous buffer ratio, cellulose I is much more abundant. By varying the organic solvent and buffer along with temperature or concentration of substrate, it could be possible to form truly unique thin films with novel glucan chain orientations. Composites with other polymers and the novel cellulose described in this invention are also possible. Some examples of other polymers are xylan, mannan, and chitin. Cellulose also could be substituted with various side chains, leading to novel polymer compounds such as cellulose acetate, cellulose butyrate, and even methylcellulose. Detergent-like celluloses, soluble in both organic and hydrophilic environments might be possible.

EXAMPLE IX

Characterization of Products

Several methods for the characterization of products synthesized in vitro, such as solubility properties, acid hydrolysis, acetolysis, specific enzymatic digestion, and linkage analysis after periodate oxidation or methylation, may be used either alone or in various combinations (Okuda et al., 1993).

Insolubility in strong alkali (e.g., 24% KOH) may be used for the detection of β-1,4-glucan, but β-1,3-glucan synthesized in vitro may also be present in the alkali-insoluble fraction (Hayashi et al., 1987). The acetic/nitric acid reagent (Updegraff, 1969) may be used for the selection of cellulose because only crystalline cellulose can remain after treatment with this reagent. The most reliable methods to prove the presence of crystalline cellulose are x-ray and electron diffraction analyses (Sarko, 1976). Highly purified cellulase conjugated to colloidal gold has also been used as a probe to identify cellulose by TEM (Lin et al., 1985).

EXAMPLE XI

Combinations of Glycosyl Transferases

Cellulase or any polysaccharide hydrolase may be used in combination with different glycosyl transferases in the aqueous mode to make heteropolymers with novel properties. For example, a heteropolymer could be synthesized by a pulsed synthesis of the β-1,4 glucan chain backbone in an organic solvent, followed by a pulsed hydrolysis or addition reaction to add a branch polysaccharide chain, then possibly back to a pulsed synthesis in organic solvent using a different enzyme to produce a linear polymer on the side chain. The combination of this type of procedures would produce a novel polysaccharide. This is similar to the method of Roth (U.S. Pat. 5,180,674, incorporated herein by reference) except that by combining organic and aqueous phases, this method can be extended to other polysaccharides such as mannans, xylans, callose, starch, etc.

Another unique property of the present invention is the use of the activated monomer in the cellulose synthesis. For example, a glucosyltransferase may be used to attach the activated monomer to the oligosaccharide. This activated terminus could then serve as a hydrolase site for further reactions. Active functional groups could include fluorine or other halogens, or methyl, allyl, trifluoroethyl and acetyl groups.

A limitation of using hydrolases exclusively is that the active site for branch formation cannot be controlled. But, having the specific glycosyltransferase available, the active side chain can be added and then a hydrolase can be used to continue the homopolymeric growth of the branch. Cyclodextrins could then be added to the ends of the branches or perhaps even proteoglycans or glycoproteins could be added to the dendritic structure.

EXAMPLE XII

Low Molecular Weight Cellooligosaccharides

Using a combination of pulsed synthesis in organic solvent and pulsed hydrolysis in aqueous medium, low molecular weight β-1,4 linked cellooligosaccharides (dp 4–200, for example) may be produced with great efficiency, and using fewer steps than the conventional synthetic reactions. The same enzyme may be used for assembly and clipping, by manipulating the environment in which the reactions take place. For example, an aqueous environment would favor the hydrolysis and a more organic environment would favor the synthesis reaction. One particular advantage of this system is that the hydrolytic enzymes are more readily available and could be used to synthesize specific bonds in the growing polymers. Low MW cellooligosaccharides are presently very expensive and must be made by acid hydrolysis of cellulose, followed by chromatographic separations. By incorporating a synthetic approach toward oligosaccharide production, the costs may be lowered, and the specificity of chain length assembly may be more accurately controlled.

Additionally, using a system related to that of Roth, glycosyl transferases may be used in conjunction with the oligosaccharide syntheses of the present invention to form complex oligosaccharides.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The following citations are incorporated in pertinent part by reference herein for the reasons cited in the above text.

REFERENCES

Blackwell, J., in *Cellulose and Other Natural Polymer Systems* (ed. Brown, R. M. Jr.), 403–428, Plenum, New York, (1982).

Brauns, D. H., J. Am. Chem. Soc. 51, 1820, (1929).
Brown, et al., 1987, E.P. application No. 87307891.9.
Brown, R. M. Jr., & Montezinos, D., Proc. Natl. Acad. Sci. U.S.A. 73,143–147, (1976).
Brown, R. M. Jr., J. Cell Sci. Suppl. 2, 13–32, (1985).
Brown, R. M. Jr., in *Cellulose and Wood-Chemistry and Technology*, (ed. Schuerch, C.) 473–492, John Wiley and Sons, New York, (1989a).
Brown, R. M. Jr., in *Cellulose: Structural and Functional Aspects*, (ed. Kennedy, J. F.), 145–151, Ellis Horwood Ltd, London, UK, (1989b).
Bureau, T. E. & Brown, R. M. Jr., Proc. Natl. Acad. U.S.A. 84, 6985–6989, (1984).
Chanzy, H., Henrissat, B., & Vuong, R., *FEBS Lett.* 172, 193–197, (1984).
Colvin, J. R., *Nature*, 183, 1135, (1959).
Delmer, D. P., *Annu. Rev. Plant Physiol.* 38, 259–290, (1987).
Elbein, A. D., Barber, G. A., & Hassid, W. Z., *J. Am. Chem. Soc.* 86, 309, (1964).
Fry, S. C., *The Growing Plant Cell Wall*: Chem. & Metabolic Analysis, Longman Scientific and Technical, Harlo, Essex., 102– 187, (1988).
Hayashi, T., Read, S. M., Drake, R. R., Haley, B. E., & Wasserman, B. P., *Plant Physiol.* 83, 1054–1062, (1987).
Hirano, S., *Agric. Biol. Chem.* 37, 187, (1973). Hussmann, E., & Muller, G., *J. M. Makromol. Chem.* 91, 212, (1966).
Itoh, T., & Brown, R. M. Jr., *Planta* 160, 372, (1984).
Klar, J., *Chem.-Ztg.* 87, 731, (1963).
Kobayashi, S., Kashiwa, K., Kawasaki, T., & Shoda, S., *J. Am. Chem. Soc.* 113, 3079–3084, (1991).
Kobayashi, S., Shoda, S., Lee, J. H., Okuda, K., Brown, R. M. Jr, & Kuga, S., Die Makromol. Chemie, manuscript submitted, (1993).
Kuga, S. and R. M. Brown in *Cellulose and Wood-Chemistry and Technology*, (ed. Schuerch, C.), 677–688, John Wiley and Sons, New York, (1989).
Kuga, S., Takagi, S., & Brown, R. M. Jr., *Polymer*, in press, (1993).
Lai, H.-L., Butler, L. G., & Axelrod, B., *Biochem. Biophys. Res. Commun.* 60, 635, (1974).
Lin, F. C., Brown, R. M. Jr., Cooper, J. B., & Delmer, D. P., *Science*, 23, 822, (1985).
Lin, F. C. & Brown, R. M. Jr., in *Cellulose and Wood-Chemistry and Technology*, (ed. Schuerch, C.), 473–492, John Wiley and Sons, New York, (1989).
Lin, F. C., Brown, R. M. Jr., Drake, R. R., Jr., & Haley, B. E., *J. Biol. Chem.* 265, 4782–4784, (1990).
Markwell, M., Bass, S. M., Bieber, L. L., & Tolbert, N. E., *Anal Biochem.*, 87, 206–210, (1978).
Mayer, R., Ross, P., Weinhouse, H., Amikan, D., Volman, G., Ohana, P., Calhoon, R. D., Wong, H. C., Emerick, W., & Benziman, M., *Proc. Natl. Acad. Sci. U.S.A.* 88, 5472–5476, (1991).
Micheel, F. Brodde, O.-E. & Reinkin, K., *Liebigs Ann. Chem.* 124, (1974).
Muller, S. C. & Brown, R. M. Jr., *J. Cell Biol.* 84, 315, (1980).
Nakatsubo, F., Takano, T., Kawada, T., & Murakami, K. in *Cellulose, Structural and Functional Aspects*, (eds. Kennedy, J. F., Philips, G. O., Williams, P. A.), Ellis Horwood, Sussex, 201–206. (1989).
Okuda, K., Li, L., Kudlicka, K., & Brown, R. M. Jr., *Plant Physiol.* 101, 1131–1142, (1993).
Preston, R. D., *The Physical Biology of Plant Cell Walls*, Chapman & Hall, London, (1974).
Rånby, B., *Acta Chemica Scandinavica*, 6, 101, (1952).
Read, S. M., & Delmer, D. P. in *Biosynthesis and Biodegradation of Cellulose*, (ed. C. H. Haigler), 177–200, Mercel Dekker, New York, (1991).
Roberts, E. M. *Biosynthesis of Cellulose II and Related Carbohydrates*, The Univ. of Texas at Austin, U.S.A. (1991).
Roelofson, P. A., *The Plant Cell*, Gebruder Borntraeger, Berlin-Nikolassee, (1959).
Ross, P., Weinhouse, H., Aloni, Y, Michaeli, D., Weinberger-Ohana, P., Mayer, R., Braun, S., de Vroom, E., van der Marel, G. A., van Boom, J. H., & Benziman, M., *Nature* 325, 279–281, (2987).
Roth, U.S. Pat. No. 5,180,674.
Sarko, A., *Appl. Polym. Syrup.* 28 (2), 729, (1976).
Sawyer, L. H. & George, W., in ref. (6), 429–455, (1982).
Saxena, I. M., Lin, F. C., & Brown, R. M., Jr., *Plant Mol. Biol.*, 15, 673–683, (1990).
Saxena, I. M., Lin, F. C., & Brown, R. M. Jr., *Plant Mol. Biol.* 16, 947–954, (1991).
Schuerch, C., *Adv. Polym. Sci.* 10, 173, (1972)
Sisson, W., *Science* 87, 350, (1938).
Uryu, T., Yamaguchi, C., Morikawa, K., Terui, K., Kanai, T., & Matsuzaki, K., *Makromolecules* 18, 599, (1985).
Updegraff, D. M., *Anal. Biochem.* 32, 420–424, (1969).
Wong, H. C., Fear, A. L., Calhoon, R. D., Eichinger, G. H., Mayer, R., Amikam, D., Ben-Bassat, A., & Tar, R., *Proc. Natl. Acad. Sci. USA*, 87, 8130–8134, (1990).
Wood, T. M., & Bhat, K. M., in *Methods for Measuring Cellulase Activities* (eds. Wood, W. A. and Kellogg, S. T.), Academic Press, Inc. San Diego, 87–112, (1988).

It is understood that those skilled in the art may practice the following claimed invention by substitution of various equivalents and that such substitutions are within the spirit and scope of these claims.

What is claimed is:

1. A method of producing cellulose I, the method comprising contacting cellobiosyl fluoride with a *Trichoderma viride* endoglucanase having an isoelectric point of about pH 3.6, obtained by the steps of:

(a) chromatography of a crude *Trichoderma viride* cellulase preparation over a polyacrylamide gel having a fractionation range of 1,500 to 20,000 daltons;

(b) isoelectric focusing; and (c) chromatography over a polyacrylamide gel having a fractionation range of 5,000 to 100,000 daltons; or alternatively, obtained by the steps of:

(d) 37%–45% ammonium sulfate fractionation of a crude *Trichoderma viride* cellulase preparation;

(e) chromatography over a polyacrylamide gel having a fractionation range of 1,500 to 20,000 daltons;

(f) isoelectric focusing; and (g) chromatography over a polyacrylamide gel having a fractionation range of 5,000 to 1000,000 daltons;

wherein said endoglucanase is contained in micelles comprising an aqueous buffer and acetonitrile in a ratio of about 2:1.

2. The method of claim 1 wherein cellulose I is produced at a cellobiosyl fluoride concentration from 5 mg/reaction to 4 mg/reaction.

3. The method of claim 1 wherein the micelles are formed in acetonitrile/aqueous buffer at a ratio of 2:1.

4. A method of synthesizing cellulose I, the method comprising the steps of:

(a) obtaining a preparation from *Trichoderma viride* cellulase having endoglucanase activity and having an isoelectric point of about pH 3.6, a molecular weight of about 39 KDa when analyzed by SDS-PAGE, in a sodium acetate buffer at pH 5;

(b) mixing said preparation with cellobiosyl fluoride in a mixture of acetonitrile and sodium acetate buffer, pH 5;

(c) stirring the resultant mixture to produce micelles; and (d) incubating at a temperature and for a time sufficient to produce cellulose I;

wherein the resultant mixture comprises acetonitrile/acetate buffer at a ratio of 2:1.

* * * * *